United States Patent [19]

Sidorenko et al.

[11] Patent Number: 4,499,904
[45] Date of Patent: Feb. 19, 1985

[54] HEART MONITORING DEVICE

[75] Inventors: Georgy I. Sidorenko; Georgy P. Lopato; Vladimir M. Yakubovich; Yaroslav G. Nikitin; Oleg I. Usachev; Anatoly P. Vorobiev, all of Minsk, U.S.S.R.

[73] Assignee: Belorussky Nauchnoissledovatelsky Institut Kardiologii, Minsk, U.S.S.R.

[21] Appl. No.: 469,036

[22] Filed: Feb. 23, 1983

[51] Int. Cl.$^3$ .............................................. A61B 5/04
[52] U.S. Cl. .................................................. 128/703
[58] Field of Search .............................. 128/702–704

[56] References Cited

U.S. PATENT DOCUMENTS

| | | | |
|---|---|---|---|
| 3,518,983 | 7/1970 | Jorgensen | 128/702 |
| 3,524,442 | 8/1970 | Horth | 128/703 |
| 3,606,882 | 9/1971 | Abe et al. | 128/704 |
| 3,618,593 | 11/1971 | Nacheu et al. | 128/702 |
| 3,654,916 | 4/1972 | Neilson | 128/702 |
| 3,658,055 | 4/1972 | Abe et al. | 128/703 |
| 3,755,783 | 8/1973 | Astarjian et al. | 128/702 |
| 3,829,766 | 8/1974 | Herz | 128/704 |
| 4,023,564 | 5/1977 | Valiquette et al. | 128/704 |
| 4,193,393 | 3/1980 | Schlager | 128/702 |
| 4,409,985 | 10/1983 | Sidorenko et al. | 128/702 |

Primary Examiner—William E. Kamm
Attorney, Agent, or Firm—Fleit, Jacobson, Cohn & Price

[57] ABSTRACT

A heart monitoring device comprises a sensing unit for detecting R-waves of an ECG signal, an ECG signal parameters determining unit responsive to the output signal of the sensing unit and producing at three outputs six signals related to features of the R-to-R intervals, a logic circuit having its inputs connected to the outputs of the ECG signal parameters determining unit, a storage unit having its inputs connected to the outputs of the logic circuit, an indication unit counting and indicating the results obtained by monitoring heart activity and having inputs connected to the outputs of the logic circuit, a timing unit having an input connected to the output of the sensing unit and outputs connected to the control inputs of the ECG signal parameters determining unit, the storage unit, and the indication unit. The ECG signal parameters determining unit, the storage unit and the indication unit are provided with reset inputs connected to a reset unit. The logic circuit is arranged to produce at its outputs eight combinations of signals depending on the signals supplied from the ECG signal parameters determining unit and from the storage unit. The indication unit indicates grouped extrasystoles, single extrasystoles, blocks, dangerous blocks, bigeminal extrasystoles, and a normal cardiac rhythm.

5 Claims, 20 Drawing Figures

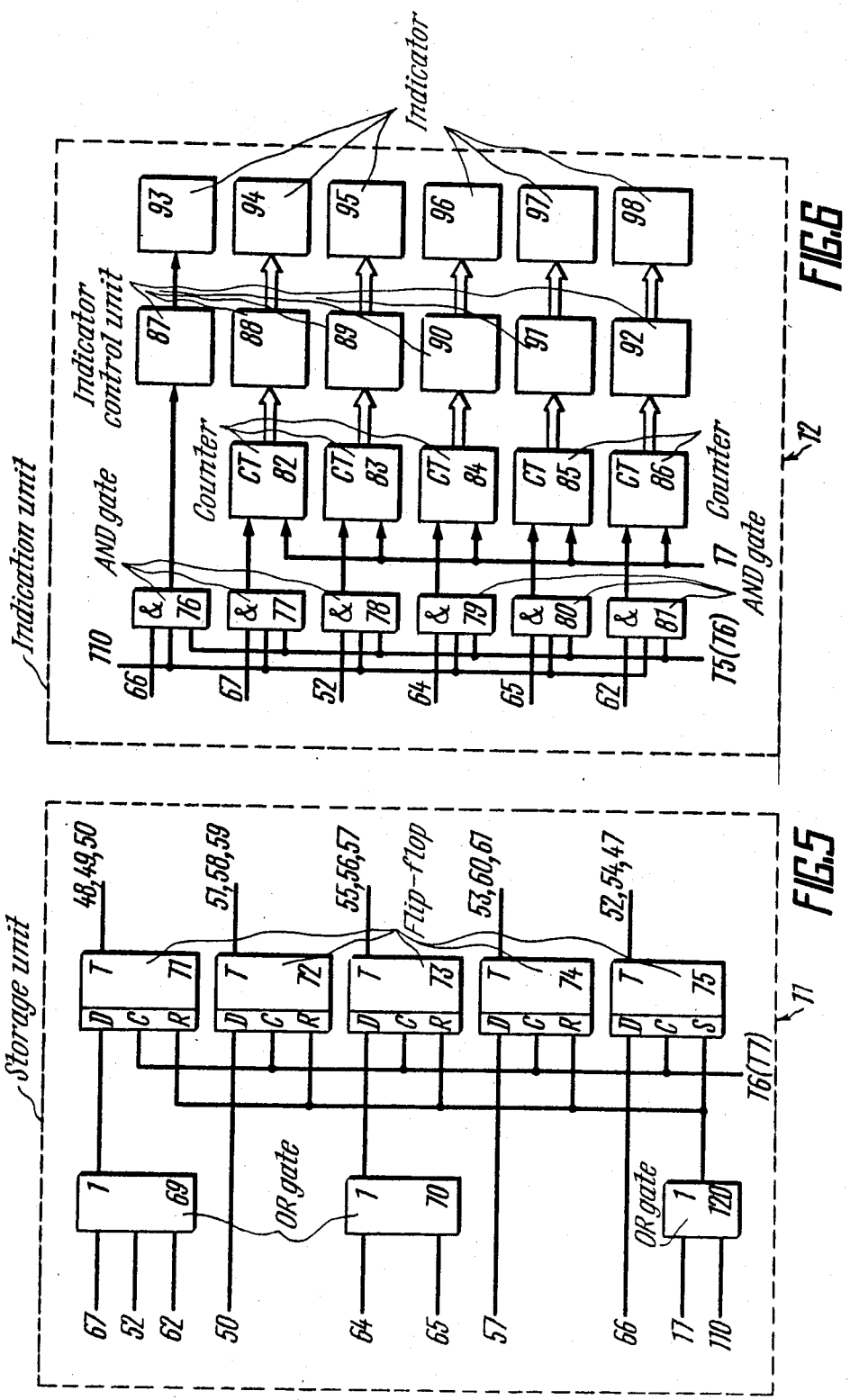

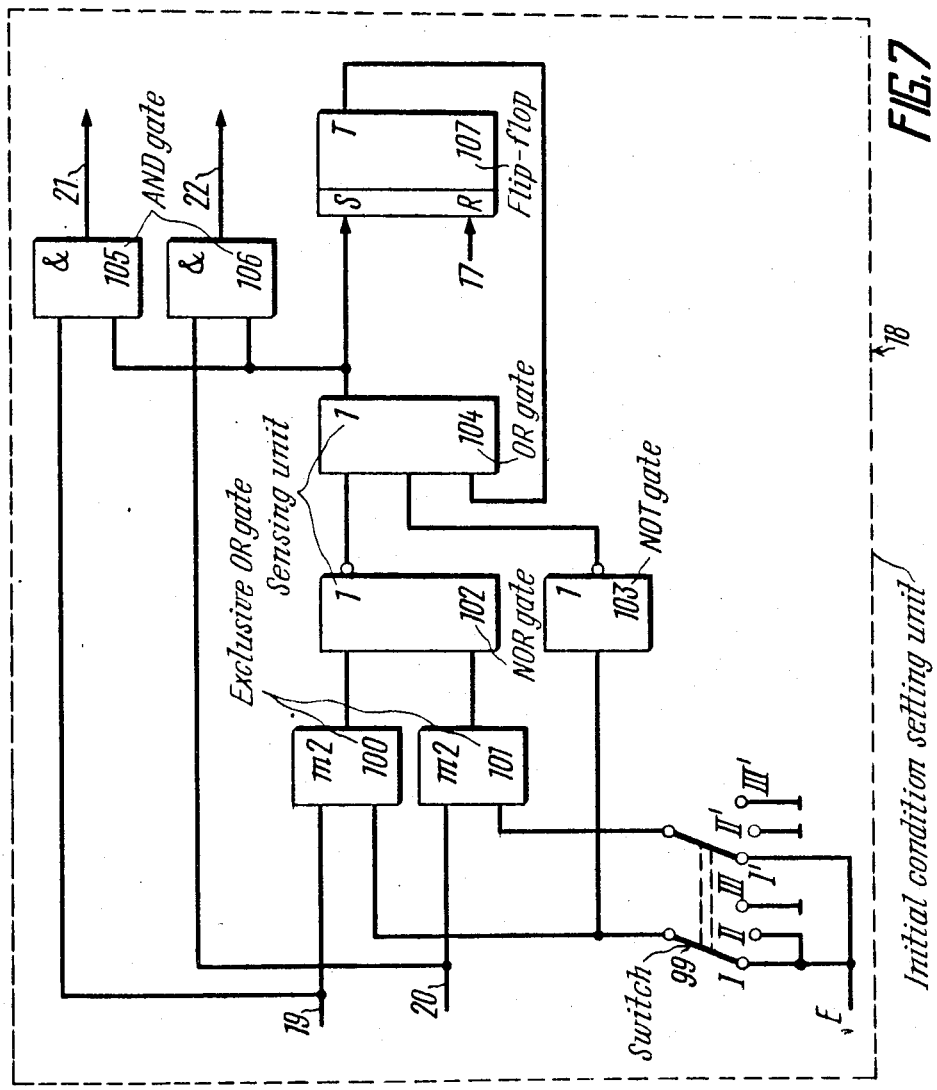

| | ⊖ | ∅ | ⊕ | |
|---|---|---|---|---|
| 71 | GE--71 | GE--71 | --72 | A |
| 72 | (5)--BIG--71<br>(6)--N--75 | N--75 | N--75 | B |
| 73 | --74 | DB--73 | DB--73 | C |
| 74 | N--75 | N--75 | N--75 | D |
| 75 | E--71 | N--75 | B--73 | E |
| | 1 | 2 | 3 | |

FIG.10

HEART MONITORING DEVICE

FIELD OF THE INVENTION

The present invention relates to diagnostic cardiologic devices, and more particularly to heart monitoring devices which can measure the time intervals between R-waves indicative of heart contractions, analyse this data and provide indication and count of irregularities in cardiac rhythm.

The present invention can be used in medical practice, for intensive monitoring of the state of a patient's cardiovascular system under resuscitation conditions, in emergency medical service, in outpatients departments, in conducting tests under physical loads during rehabilitation procedure, and for observing a person's behaviour under extreme conditions (in aviation, space and sports medicine).

BACKGROUND OF THE INVENTION

More than 250,000 heart attack victims die each year without having reached the hospital. If all of these victims had been able to get to a hospital and receive proper treatment, a substantial number of them would be alive today. The greatest single factor in these people not reaching a hospital in time to receive help is the apparent inability of the person to reach a decision of whether or not to call for help. One reason for this long decision time is the inability of the patient to properly monitor his heart rate and cardiac rhythm, which, in turn, is due to the lack of equipment necessary to do this.

It has been found that at the onset of a heart attack, the heart rate and cardiac rhythm are usually disturbed and the heartbeat contains a number of dangerous arrhythmias, or irregular beat signs, which, if detected in time, would give a good indication of an impending or recently occurring heart attack. These arrhythmias are usually of the type of a premature ventricular contraction (extrasystoles, blocks, bradycardia and tachycardia).

These arrhythmias give an indication of a possible impending terminal states: ventricular fibrillation and asystolia.

It should be noted that the above mentioned arrhythmias are directly related to the time intervals between heartbeats. These intervals can readily be determined by measuring the time between successive R-waves of the cardiac signal, with subsequent processing of this information to arrive at data indicating one or more of these symptoms.

The employment of a heart monitoring device makes it possible to offer necessary help in proper time and thus to reduce the occurrence rate of dangerous conditions.

Known is a heart monitoring device (cf. U.S. Pat. No. 4,006,737), comprising comparison circuits having first inputs supplied with an electrocardiograph (ECG) signal and second inputs supplied with constant preset signals corresponding to preset time and amplitude values. The outputs of the comparison circuits are connected through AND gates to accumulating devices whose inputs are connected to indication units.

Such a device provides detection and accumulation of only two kinds of heartbeat irregularities, i.e. premature ventricular contractions and supraventricular tachycardia. In addition, such a device can indicate when the heart rate has passed an upper or lower predetermined limit.

This device, however, offers only limited diagnostic possibilities, because the time and amplitude parameters of the ECG signal are compared to constant preset values, with the result that the dynamics of normal changes in the heart rate caused by physical or emotional strains cannot be taken into consideration. This, in turn, creates a potential possibility for false conclusions concerning irregularities in the heartbeat.

Known is a cardiac arrhythmia detector (cf. U.S. Pat. No. 3,861,387), comprising a unit for generating the first time derivative of an ECG signal, a unit for measuring the peak amplitudes of the first time derivative signal, a unit for establishing the running average of the peak amplitudes of the first time derivative signal over a predetermined time period, a unit for measuring time intervals between the peaks of the first time derivative signal, a unit for establishing the running average of the time intervals between the peaks of the first time derivative signal over a predetermined time period, a comparison circuit operating when the peak amplitude of the first time derivative signal deviates from the average amplitude value by ±25%, a second comparison circuit operating when the time interval between the peaks of the time derivative signal deviates from the average interval value by ±25%, and missing heartbeats detecting unit including means for measuring the time intervals between the R-waves of the ECG signal and means for declaring a missing heartbeat when the current interval is 1,5 times greater than the immediately preceding interval.

This arrhythmia detector ensures a more reliable detection of irregularities in the heartbeat, such as abnormal ventricular contractions, irregularities in cardiac rhythm accompanied by lengthening of RR intervals, and irregularities in the heart rate.

Such an arrhythmia detector, however, does not provide separate accumulation of detected irregularities and does not classify them as separate groups, but only indicates the fact of occurrence of the above-mentioned irregularities in the heart rate and cardiac rhythm.

Known is a heart monitoring device (cf. U.S. Pat. No. 3,633,569), comprising an ECG signal amplification unit, an arrhythmia detector, a bradycardia detector, a tachycardia detector, an accumulating counter for counting the detected irregularities, and a 16-digit binary indication unit.

This device detects arrhythmias whenever the difference between the durations of two successive RR intervals exceeds a constant preset value of 120 ms. In addition, such a device detects bradycardia or tachycardia when the heart rate goes beyond an upper or lower preset value.

However, since the difference between the durations of two successive intervals is compared to a constant preset value (120 ms), the dynamics of normal changes in the heart rate under different conditions are not taken into account. This leads to substantial increase in the number of false positive conclusions in case of bradycardia and of false negative conclusions in case of tachycardia.

Besides, such a device does not distinguish between different kinds of irregularities in the heart rate and cardiac rhythm, but only calculates the total number of irregularities and indicates this number in binary code, which is difficult to read.

Known is a heart monitoring device (cf. U.S. Pat. No. 3,881,467), comprising a unit for detecting R-waves of an ECG signal, an ECG signal parameters determining unit having its input connected to the R-waves detecting unit, an indication unit having its inputs connected to the ECG signal parameters determining unit, a timing circuit having its input connected to the output of the R-wave detecting unit and its output connected to the control input of the ECG signal parameters determining unit.

The ECG signal parameters determining unit generates signals in accordance with data obtained by comparing the durations of time intervals between the R-waves of the ECG signal.

In this device the duration of the last occurring interval $RR_i$ between the R-waves is compared to the duration of a previous normal interval $RR_N$.

The last occurring interval becomes the previous normal interval for the subsequent comparisons only when it constitutes at least a predetermined percentage of the previous normal interval.

If the condition $$RR_i < 0.8 RR_N \qquad (1)$$

is satisfied, then an extrasystole is registered.

If $$RR_i > 1.2 RR_N, \qquad (2)$$

then a missing heart beat is declared.

If irregularity in cardiac rhythm is detected, i.e. if the condition (1) or (2) is satisfied, the interval between the second and the third heartbeats following the irregular heartbeat is taken as the normal interval for the subsequent comparisons. Besides, an interval following four consecutive widened RR intervals is also regarded as a normal interval.

This heart monitoring device provides detection and count of extrasystoles.

However, by comparing the duration of the last occurring interval to the duration of the so-called "normal" interval, it is often possible to come to false conclusions concerning the number of extrasystoles.

Besides, the conclusion concerning the presence of irregularity in cardiac rhythm is drawn with no regard for the relation between the durations of intervals preceding those being considered.

As a result, when the frequency of occurrence of extrasystoles increases, the number of extrasystolic cardiac contractions is determined incorrectly.

Certain combinations of intervals with skipped beats may cause the device to register extrasystoles when they are actually absent.

The device can detect and count only simple cases of isolated extrasystoles, while the potentially dangerous facts of bigeminies, grouped extrasystoles and blocks are not detected.

Known is a heart monitoring device (cf. U.S. Pat. No. 3,658,055), comprising a unit for detecting R-waves of an ECG signal, and an ECG signal parameters determining unit responsive to the signal at the output of the R-waves detecting unit. The ECG signal parameters determining unit is arranged to produce at a first output a first signal when the magnitude of the difference between the duration of the last occurring interval between the R-waves of the ECG signal and the duration of the preceding interval is smaller than a predetermined percentage of the duration of the last occurring interval, to produce at the first output a second signal when the magnitude of the difference between the duration of the last occurring interval between the R-waves and the duration of the preceding interval is greater than, or equal to, said predetermined percentage of the duration of the last occurring interval, to produce at a second output a first signal when the duration of the last occurring interval between the R-waves is smaller than the duration of the preceding interval, and to produce at the second output a second signal when the duration of the last occurring interval between the R-waves is greater than, or equal to, the duration of the preceding interval. The outputs of the ECG signal parameters determining unit are connected to logic circuits, the outputs of which are connected to the inputs of a storage unit and to the inputs of an indication unit arranged to count and indicate the results obtained by monitoring the heart activity.

The output of the R-waves detecting unit is connected to the input of a timing circuit whose outputs are respectively connected to the control inputs of the ECG signal parameters determining unit, the storage unit and the indication unit.

If $RR_n/RR_{n-1} > 1.2$ (where "n" and "n−1", are, respectively, the serial numbers of the last occurring cardiac cycle and the cardiac cycle preceding the last occurring cycle), the code $RR_f$ is developed. When $RR_n/RR_{n-1} < 0.85$, the code $RR_s$ is developed. The combination of such codes is stored for several (e.g. four) successive cardiac cycles, the number of which is determined by the detected irregularity in the cardiac rhythm. To diagnose the irregularities in the cardiac rhythm, the stored data is analysed in the logic circuits according to characteristics determined by experience of clinical diagnosis. When all the characteristics corresponding to a certain type of arrhythmia are present, a corresponding logic circuit operates producing a signal indicative of this type of arrhythmia.

Thus, by coding the RR intervals, storing the codes for several successive cardiac cycles and logically analysing the stored data, the device makes it possible to monitor (diagnose) the heart activity.

However, to obtain such a diagnosis of irregularities in cardiac rhythm, the number of the analysed intervals should be no less than three.

When it is necessary to diagnose complicated arrhythmias, such as bigeminies, grouped extrasystoles, and the like, the required number of RR intervals to be analysed substantially increases. In such cases, to diagnose irregularities in cardiac rhythm, a considerable amount of data must be processed, because the number of different combinations of the developed codes corresponding to different heart deseases, becomes very great. Since each of said combinations is analysed by a corresponding logic circuit, the circuit design of the heart monitoring device becomes very complicated, with the result that the implementation and employment of the device become difficult.

SUMMARY OF THE INVENTION

It is an object of the present invention to provide a heart monitoring device which makes possible prolonged and continuous monitoring of various types of irregularities in the heart rate and cardiac rhythm of a person during treatment of cardiovascular deseases, rehabilitation, tests under physical loads, and during extreme conditions.

It is another object of the present invention to provide a heart monitoring device which simplifies monitoring of heart activity by reducing the amount of the processed data.

It is still another object of the present invention to provide a heart monitoring device which is capable of counting and indicating in decimal code the number of occurrences of each of the detected irregularities in the heart rate and cardiac rhythm.

It is still another object of the present invention to provide a heart monitoring device which ensures more reliable detection of irregularities in the heart rate and cardiac rhythm by providing automatic self-check on the device operation.

It is still another object of the present invention to provide a heart monitoring device which makes it possible to prevent incorrect diagnosis of irregularities in the heart rate and cardiac rhythm when the analysis is started with an irregular time interval between R-waves of the ECG signal.

The principal object of the present invention is to provide a heart monitoring device which makes possible simplification of monitoring of heart activity by reducing the amount of the processed data.

With this principal object in view there is provided a heart monitoring device comprising a sensing unit for detecting R-waves of an ECG signal, an ECG signal parameters determining unit responsive to the output signal of the sensing unit to produce at its first output a first signal when the magnitude of the difference between the duration of the last occurring interval between the R-waves of the ECG signal and the duration of the interval between the R-waves of the ECG signal immediately preceding the last occurring interval is smaller than a predetermined percentage of the duration of the last occurring interval, and a second signal when the magnitude of the difference between the duration of the last occurring interval between the R-waves of the ECG signal and the duration of the interval between the R-waves of the ECG signal immediately preceding the last occurring interval is greater than, or equal to, said predetermined percentage of the duration of the last occurring interval, and to produce at its second output a first signal when the duration of the last occurring interval between the R-waves of the ECG signal is smaller than the duration of the interval between the R-waves of the ECG signal immediately preceding the last occurring interval, and a second signal when the duration of the last occurring interval between the R-waves of the ECG signal is greater than, or equal to, the duration of the interval immediately preceding the last occurring interval, a logic circuit having its first input connected to the first output of the ECG signal parameters determining unit, its second input connected to the second output of the ECG signal parameters determining unit, a storage unit having its inputs connected to the outputs of the logic circuit, an indication unit counting and indicating the results obtained by monitoring heart activity and having its inputs connected to the outputs of the logic circuit, a timing unit having an input connected to the output of the sensing unit, a first output connected to the control input of the storage unit, a second output connected to the control input of the indication unit and a plurality of outputs connected to the control inputs of the ECG signal parameters determining unit, in which heart monitoring device, according to the invention, the ECG signal determining unit is further provided with a third output to produce thereat a first signal when the difference between the duration of the last occurring interval between the R-waves of the ECG signal and the duration of the interval between the R-waves of the ECG signal immediately preceding the interval immediately preceding the last occurring interval is smaller than a predetermined value, and a second signal when the difference between the duration of the last occurring interval between the R-waves of the ECG signal and the duration of the interval between the R-waves of the ECG signal immediately preceding the interval immediately preceding the last occurring interval is greater than, or equal to, said predetermined value, the logic circuit is further provided with a third input connected to the third output of the ECG signal parameters determining unit and with a plurality of inputs connected to the outputs of the storage unit, the reset inputs of the ECG signal parameters determining unit, of the storage unit and of the indication unit are connected to a reset unit, the logic circuit being arranged to produce at its outputs a first combination of signals when its first input is supplied with the second signal from the first output of the ECG signal parameters determining unit, its second input is supplied with the first signal from the second output of the ECG signal parameters determining unit and the code stored in the storage unit corresponds to the first, a third or an eighth combination of signals at the outputs of the logic circuit, the logic circuit being arranged to produce at its outputs the first combination of signals when its first input is supplied with the first signal from the first output of the ECG signal parameters determining unit and the code stored in the storage unit corresponds to the first, the third or the eighth combination of signals at the outputs of the logic circuit, the logic circuit being arranged to produce at its outputs a second combination of signals when its first input is supplied with the second signal from the first output of the ECG signal parameters determining unit, its second input is supplied with the second signal from the second output of the ECG signal parameters determining unit and the code stored in the storage unit corresponds to the first, the third or the eighth combination of signals at the outputs of the logic circuit, the logic circuit being arranged to produce at its outputs the third combination of signals when its first input is supplied with the second signal from the first output of the ECG signal determining unit, its second input is supplied with the first signal from the second output of the ECG signal parameters determining unit and the code stored in the storage unit corresponds to a seventh combination of signals at the outputs of the logic circuit, the logic circuit being arranged to produce at its outputs a fourth combination of signals when its first input is supplied with the second signal from the first output of the ECG signal parameters determining unit and its second input is supplied with the second signal from the second output of the ECG signal parameters determining unit and the code stored in the storage unit corresponds to a sixth or to the seventh combination of signals at the outputs of the logic circuit, the logic circuit being arranged to produce at its outputs a fifth combination of signals when its first input is supplied with the second signal from the first output of the ECG signal parameters determining unit, its second input is supplied with the second signal from the second output of the ECG signal parameters determining unit and the code stored in the storage unit corresponds to the fourth or fifth combination of signals at the output of the logic circuit, the logic circuit being arranged to produce at its outputs the fifth combination of signals when its first input is supplied with the first signal from the first output of the ECG signal parameters determining unit and the code stored in the storage unit corresponds to the fourth or fifth combination of signals at the outputs of the logic circuit, the logic circuit being arranged to produce at its outputs the sixth combination of signals when its first input is supplied with the second signal from the first output of the ECG signal parameters determimimg unit, its second input is supplied with the first signal from the second output of the ECG signal parameters determining unit and the code stored in the storage unit corresponds to the fourth of fifth combination of signals at the outputs of the logic circuit, the logic circuit being arranged to produce at its output the seventh combination of signals when its first input is supplied with the second signal from the first output of the ECG signal parameters determining unit, its second input is supplied with the second signal from the second output of the ECG signal parameters determining unit and the code stored in the storage unit corresponds to the second combination of signals at the outputs of the logic circuit, the logic circuit being arranged to produce at its outputs the seventh combination of signals when its first input is supplied with the first signal from the first output of the ECG signal parameters determining unit and the code stored in the storage unit corresponds to the second combination of signals at the outputs of the logic circuit, the logic circuit being arranged to produce at its outputs the seventh combination of signals when its first input is supplied with the second signal from the first output of the ECG signal parameters determining unit, its second input is supplied with the first signal from the second output of the ECG signal parameters determining unit, its third input is supplied with the second signal from the third output of the ECG signal parameters determining unit and the code stored in the storage unit corresponds to the second combination of signals at the outputs of the logic circuit, the logic circuit being arranged to produce at its outputs the seventh combination of signals when its first input is supplied with the first signal from the first output of the ECG signal parameters determining unit and the code stored in the storage unit corresponds to the sixth or seventh combination of signals at the outputs of the logic circuit, the logic circuit being arranged to produce at its outputs the seventh combination of signals when its first input is supplied with the second signal from the first output of the ECG signal parameters determining unit, its second input is supplied with the first signal from the second output of the ECG signal parameters determining unit and the code stored in the storage unit corresponds to the sixth combination of signals at the outputs of the logic circuit, the logic circuit being arranged to produce at its outputs the eighth combination of signals when its first input is supplied with the second signal from the first output of the ECG signal parameters determining unit, its second input is supplied with the first signal from the second output of the ECG signal parameters determining unit, its third input is supplied with the first signal from the third output of the ECG signal parameters determining unit and the code stored in the storage unit corresponds to the second combination of signals at the outputs of the logic circuit, the indication unit being arranged to indicate grouped extrasystoles, single extrasystoles, blocks, dangerous blocks, bigeminies and a normal cardiac rhythm, the indication unit indicating a grouped extrasystole when the logic circuit produces at its outputs the first combination of signals, a single extrasystole when the logic circuit produces at its outputs the third combination of signals, a block when the logic circuit produces at its outputs the fourth combination of signals, a dangerous block when the logic circuit produces at its outputs the fifth combination of signals, a bigeminal extrasystole when the logic circuit produces at its output the eighth combination of signals, and a normal cardiac rhythm when the logic circuit produces at its outputs the seventh combination of signals.

In the proposed device the signals developed at the third output of the ECG signal parameters determining unit during each cycle of analysis of the ECG signal are obtained by comparing the difference between the duration of the last occurring interval ($RR_i$) between the R-waves of the ECG signal and the duration of the interval ($RR_{i-2}$) preceding that occurring before the last occurring interval to a predetermined constant value. By this means it is possible to distinguish bigeminy, at which the interval following an extrasystole is practically the same as the interval preceding the extrasystolic interval, from transition to a normal heartbeat after a signal extrasystole or grouped extrasystoles, when the interval following the last extrasystole (compensatory pause) is much greater than the interval preceding the last extrasystole.

The combinations of signals developed at the outputs of the logic circuit during each cycle of analysis of the ECG signal are obtained by analysing signals from the outputs of the ECG signal parameters determining unit and from the outputs of the storage unit. By this means it is possible to classify irregularities in cardiac rhythm into groups or to draw an intermediate conclusion concerning cardiac rhythm, which conclusion is not indicated but is used for drawing the final conclusion in the following cycle of analysis. In doing so, the cardiac rhythm is classified on the basis of data obtained by comparing the last occurring interval between the R-waves of the ECG signal to one or two preceding intervals, with regard for that conclusion concerning the cardiac rhythm which was made in the preceding cycle of analysis and which includes data on the cardiac rhythm that existed before the beginning of analysis.

As a result, only three data parameters are analysed: (1) the relation between the duration of the last occurring interval between the R-waves of the ECG signal and the duration of the interval preceding the last occurring interval, (2) the relation between the duration of the last occurring interval and the duration of the interval preceding that occurring before the last occurring interval, and (3) the conclusion concerning cardiac rhythm and drawn in the preceding cycle of analysis of the ECG signal. Since this conclusion carries in a condensed form data concerning the cardiac rhythm that existed before the time of analysis, the next-in-turn conclusion is drawn on the basis of sufficiently full data on cardiac rhythm. In such a case the amount of the processed data is not large.

The introduction of the reset unit into the heart monitoring device makes possible application of a reset signal to the reset inputs of the ECG signal parameters determining unit, the storage unit and the indication unit. On application of the reset signal, the ECG signal parameters determining unit and the storage unit are set to a normal cardiac rhythm, while the indication unit is prepared for analysing the coming data. The reset signal remains at the reset inputs of the ECG signal parameters determining unit, the storage unit and the indication unit for a time period during which at least three RR intervals take place, so that the ECG signal parameters determining unit is allowed to develop data required for analysis.

It is expedient to provide the heart monitoring device with an initial condition setting unit arranged to be set to one of three positions and having a first input connected to the first output of the ECG signal parameters determining unit, a second input connected to the second output of the ECG signal parameters determining unit, a reset input connected to the output of the reset unit, a first output connected to the first input of the logic circuit, and a second output connected to the second input of the logic circuit. When set to a first position, the initial condition setting unit produces at its first output a signal equal to the first signal at the first output of the ECG signal determining unit and at its second output a signal equal to the first signal at the second output of the ECG signal parameters determining unit, if the first input of the initial condition setting unit is supplied with the first signal from the first output of the ECG signal parameters determining unit and the second input of the initial condition setting unit is supplied with the first signal from the second output of the ECG signal parameters determining unit, or if the first input of the initial condition setting unit is supplied with the first signal from the first output of the ECG signal parameters determining unit and the second input of the initial condition setting unit is supplied with the second signal from the second output of the ECG signal parameters determining unit, or if the first input of the initial condition setting unit is supplied with the second signal from the first output of the ECG signal parameters determining unit and the second input of the initial condition setting unit is supplied with the first signal from the second output of the ECG signal parameters determining unit. This takes place until the first input of the initial condition setting unit is supplied for the first time with the second signal from the first output of the ECG signal parameters determining unit and the second input of the initial condition setting unit is simultaneously supplied with the second signal from the second output of the ECG signal parameters determining unit, whereupon the initial condition setting unit produces at its first output a signal equal to the signal at its first input and at its second output a signal equal to the signal at its second input. When set to a second position, the initial condition setting unit produces at its first output a signal equal to the first signal at the first output of the ECG signal parameters determining unit and at its second output a signal equal to the first signal at the second output of the ECG signal parameters determining unit, if the first input of the initial condition setting unit is supplied with the first signal from the first output of the ECG signal parameters determining unit and the second input of the initial condition setting unit is supplied with the first signal from the second output of the ECG signal parameters determining unit, or if the first input of the initial condition setting unit is supplied with the first signal from the first output of the ECG signal parameters determining unit and the second input of the initial condition setting unit is supplied with the second signal from the second output of the ECG signal parameters determining unit, or if the first input of the initial condition setting unit is supplied with the second signal from the first output of the ECG signal parameters determining unit and the second input of the initial condition setting unit is supplied with the second signal from the second output of the ECG signal parameters determining unit. This takes place until the first input of the initial condition setting unit is supplied for the first time with the second signal from the first output of the ECG signal parameters determining unit and the second input of the initial condition setting unit is simultaneously supplied with the first signal from the second output of the ECG signal parameters determining unit, whereupon the initial condition setting unit produces at its first output a signal equal to the signal at its first input and at its second output a signal equal to the signal at its second input. When set to a third position, the initial condition setting unit produces at its outputs signals respectively equal to the signals at its inputs.

The introduction of the initial condition setting unit into the circuit makes it possible to eliminate the possibility of erroneous operation of the device in the beginning of analysis of the ECG signal after the device is turned on. In case of a disturbed cardiac rhythm, an irregular interval between the R-waves of the ECG signal (extrasystolic, corresponding to a block, or compensatory) may appear upon turning on the device. In such an event, when the duration of the irregular interval is compared to the duration of the following interval, false conclusions concerning cardiac rhythm will be drawn.

The setting of initial conditions makes it possible for the analysis of cardiac rhythm to begin only under certain circumstances excluding erroneous operation of the heart monitoring device, i.e. when the change in the duration of an RR interval in relation to the duration of the preceding interval corresponds to the cardiac rhythm which is typical of the person being studied. The initial conditions are set by a physician on the basis of the previously obtained data on the person's cardiac rhythm (by studying electrocardiograms, watching the ECG signal on the screen of an oscilloscope, etc.).

In case of frequent appearance of lengthened RR intervals corresponding to skipped ventricular contractions, the initial condition setting unit is set to the first position. In such a case the analysis of cardiac rhythm is started only at the appearance of a set of characteristics corresponding to lengthening of the last occurring interval in relation to the preceding interval.

In case of frequent appearance of shortened RR intervals corresponding to bigeminy or to grouped or frequent single extrasystoles, the initial condition setting unit is set to the second position. In such a case the analysis of cardiac rhythm is started only at the appearance of a set of characteristics corresponding to shortening of the last occurring interval in relation to the preceding interval.

In case of a regular cardiac rhythm or when rare single arrhythmias occur against the background of a regular cardiac rhythm and the probability of starting the analysis of the ECG signal with an RR interval changed in duration is small, the initial setting unit is set to the third position. In such a case the analysis of cardiac rhythm is started as soon as the device is turned on.

According to one embodiment of the invention the logic circuit comprises a first AND gate having a first input connected to the first output of the ECG signal parameters determining unit and a second input connected to the second output of the ECG signal parameters determining unit, a second AND gate having an input connected to the first output of the ECG signal parameters determining unit and an inverting input connected to the second output of the ECG signal parameters determining unit, a NOT gate having an input connected to the first output of the ECG signal parameters determining unit, a third AND gate having a first input connected to the output of the second AND gate, a fourth AND gate having a first input connected to the output of the NOT gate, a fifth AND gate having a first input connected to the output of the first AND gate, a sixth AND gate having a first input connected to the output of the second AND gate, a seventh AND gate having a first input connected to the output of the second AND gate, an eighth AND gate having a first input connected to the output of the first AND gate, a ninth AND gate having a first input connected to the output of the first AND gate, a tenth AND gate having a first input connected to the output of the first AND gate, an eleventh AND gate having a first input connected to the output of the NOT gate, a twelfth AND gate having a first input connected to the output of the second AND gate, a thirteenth AND gate having a first input connected to the output of the NOT gate, a fourteenth AND gate having a first input connected to the output of the first AND gate, a fifteenth AND gate having a first input connected to the output of the second AND gate, sixteenth AND gate having a first input connected to the output of the NOT gate, a seventeenth AND gate having a first input connected to the output of the NOT gate, an eighteenth AND gate having an inverting input connected to the third output of the ECG signal parameters determining unit and a second input connected to the output of the sixth AND gate, a ninteenth AND gate having a first input connected to the third output of the ECG signal parameters determining unit and a second input connected to the output of the sixth AND gate, a first OR gate having a first input connected to the output of the third AND gate and a second input connected to the output of the fourth AND gate, a second OR gate having a first input connected to the output of the eighth AND gate and a second input connected to the output of the ninth AND gate, a third OR gate having a first input connected to the output of the tenth AND gate and a second input connected to the output of the eleventh AND gate, and a fourth OR gate having a first input connected to the output of the thirteenth AND gate, a second input connected to the output of the fourteenth AND gate, a third input connected to the output of the fifteenth AND gate, a fourth input connected to the output of the sixteenth AND gate, a fifth input connected to the output of the seventeenth AND gate and a sixth input connected to the output of the nineteenth AND gate. The storage unit comprises a first OR gate having a first input connected to the output of the first OR gate of the logic circuit, a second input connected to the output of the seventh AND gate of the logic circuit and a third input connected to the output of the eighteenth AND gate of the logic circuit, a second OR gate having a first input connected to the output of the second OR gate of the logic circuit and a second input connected to the output of the third OR gate of the logic circuit, a first flip-flop having a data input connected to the output of the first OR gate of the storage unit, a clock input connected to the first output of the timing unit, a reset input connected to the output of the reset unit and an output connected to second inputs of the third, fourth and fifth AND gates of the logic circuit, a second flip-flop having a data input connected to the output of the fifth AND gate of the logic circuit, a clock input connected to the first output of the timing unit, a reset input connected to the output of the reset unit and an output connected to second inputs of the sixth, thirteenth and fourteenth AND gates of the logic circuit, a third flip-flop having a data input connected to the output of the second OR gate of the storage unit, a clock input connected to the first output of the timing unit, a reset input connected to the output of the reset unit and an output connected to second inputs of the tenth, eleventh and twelfth AND gates of the logic circuit, a fourth flip-flop having a data input connected to the output of the twelfth AND gate of the logic circuit, a clock input connected to the first output of the timing unit, a reset input connected to the output of the reset unit and an output connected to second inputs of the eighth, fifteenth and sixteenth AND gates of the logic circuit, and a fifth flip-flop having a data input connected to the output of the fourth OR gate of the logic circuit, a clock input connected to the first output of the timing unit and an output connected to second inputs of the seventh, ninth and seventeenth AND gates of the logic circuit. The indication unit comprises a first AND gate having a first input connected to the output of the fourth OR gate of the logic circuit, a second input connected to the second output of the timing unit, a second AND gate having a first input connected to the output of the first OR gate of the logic circuit and a second input connected to the second output of the timing unit, a third AND gate having a first input connected to the output of the seventh AND gate of the logic circuit and a second input connected to the second output of the timing unit, a fourth AND gate having a first input connected to the output of the second OR gate of the logic circuit and a second input connected to the second output of the timing unit, a fifth AND gate having a first input connected to the output of the third OR gate of the logic circuit and a second input connected to the second output of the timing unit, a sixth AND gate having a first input connected to the output of the eighteenth AND gate of the logic circuit and a second input connected to the second output of the timing unit, a first counter having a counting input connected to the output of the second AND gate of the indication unit and a reset input connected to the output of the reset unit, a second counter having a counting input connected to the output of the third AND gate of the indication unit and a reset input connected to the output of the reset unit, a third counter having a counting input connected to the output of the fourth AND gate of the indication unit and a reset input connected to the output of the reset unit, a fourth counter having a counting input connected to the output of the fifth AND gate of the indication unit and a reset input connected to the output of the reset unit, a fifth counter having a counting input connected to the output of the sixth AND gate of the indication unit and a reset input connected to the output of the reset unit, a first indicator control unit having an input connected to the output of the first AND gate of the indication unit, a second indicator control unit having inputs connected to the outputs of the first counter, a third indicator control unit having inputs connected to the outputs of the second counter, a fourth indicator control unit having inputs connected to the outputs of the third counter, a fifth indicator control unit having inputs connected to the outputs of the fourth counter, a sixth indicator control unit having inputs connected to the outputs of the fifth counter, a first indicator indicating a normal cardiac rhythm and having an input connected to the output of the first indicator control unit, a second indicator indicating the number of grouped extrasystoles and having inputs connected to the outputs of the second indicator control unit, a third indicator indicating the number of single extrasystoles and having inputs connected to the outputs of the third indicator control unit, a fourth indicator indicating the number of blocks and having inputs connected to the outputs of the fourth indicator control unit, a fifth indicator indicating the number of dangerous blocks and having inputs connected to the outputs of the fifth indicator control unit, and a sixth indicator indicating the number of bigeminal extrasystoles and having inputs connected to the outputs of the sixth indicator control unit.

According to another embodiment of the invention, the initial condition setting unit comprises a first Exclusive OR gate having a first input constituting the first input of the initial condition setting unit, a second Exclusive OR gate having a first input constituting the second input of the initial condition setting unit, a NOR gate having a first input and a second input respectively connected to the outputs of the first and second Exclusive OR gates, a NOT gate having an input connected to a second input of the first Exclusive OR gate, an OR gate having a first input connected to the output of the NOR gate and a second input connected to the output of the NOT gate, a first AND gate having a first input connected to the first input of the first Exclusive OR gate, a second input connected to the output of the OR gate and an output constituting the first output of the initial condition setting unit, a second AND gate having a first input connected to the first input of the second Exclusive OR gate, a second input connected to the output of the OR gate and an output constituting the second output of the initial condition setting unit, a flip-flop having a set input connected to the output of the OR gate, a reset input connected to the output of the reset unit and an output connected to a third input of the OR gate, and a switch. When the switch is set to a first position, the second input of the first Exclusive OR gate is supplied with a signal equal to the second signal at the first output of the ECG signal parameters determining unit and the second input of the second Exclusive OR gate is supplied with a signal equal to the second signal at the second output of the ECG signal parameters determining unit. When the switch is set to a second position, the second input of the first Exclusive OR gate is supplied with a signal equal to the second signal at the first output of the ECG signal parameters determining unit and the second input of the second Exclusive OR gate is supplied with a signal equal to the first signal at the second output of the ECG signal parameters determining unit. When the switch is set to a third position, the input of the NOT gate is supplied with a signal equal to the first signal at the first output of the ECG signal parameters determining unit.

According to still another embodiment of the invention, the heart monitoring device further comprises a monostable multivibrator having an input connected to an additional output of the timing unit and an output connected to a second input of the timing unit, a pulse oscillator having an enable input connected to the additional output of the timing unit, a disable input connected to the output of the monostable multivibrator and an output connected to a second input of the ECG signal parameters determining unit, a flip-flop having a data input connected to a fourth output of the ECG signal parameters determining unit, a set input and a clock input each connected to two outputs of said plurality of outputs of the timing unit connected to the control inputs of the ECG signal parameters determining unit, an inverted output connected to a second reset input of the storage unit and a direct output connected to the indication permitting input of the indication unit, and a malfunction indicator having an input connected to the inverted output of the flip-flop.

The introduction of the monostable multivibrator, the pulse oscillator, the flip-flop and the malfunction indicator into the circuit of the heart monitoring device makes it possible to provide automatic check on the operation of the basic device units, i.e. the sensing unit, the ECG signal parameters determining unit and the timing unit, which units determine the correctness of measurements and of comparison between the time parameters of the ECG signal. The check is performed after each cycle of analysis of cardiac rhythm by generating a test arrhythmia, the detection of which confirms the operability of the basic units. If the device fails to detect the test arrhythmia, a malfunction signal is generated and indicated, and the storage unit is stored with a combination of signals corresponding to the normal cardiac rhythm, after which the analysis of the cardiac rhythm is performed with reference to this combination.

The invention is further explained by a detailed description of its preferred embodiments with reference to the accompanying drawings.

The aforementioned and other objects and advantages of the present invention will become more apparent upon consideration of the following detailed description of the preferred embodiments taken in conjunction with the accompanying drawings.

BRIEF DESCRIPTION OF THE DRAWINGS

FIG. 5 is a block diagram of the storage unit, according to the preferred embodiment of the invention;

FIG. 6 is a block diagram of the indication unit, according to the preferred embodiment of the invention;

FIG. 7 is a block diagram of the initial condition setting unit, according to the preferred embodiment of the invention;

FIG. 10 is a table illustrating changes in the states of the storage unit flip-flops brought about by logical signals appearing at the lines of the ECG signal parameters determining unit;

DETAILED DESCRIPTION OF THE INVENTION

Figure 1:
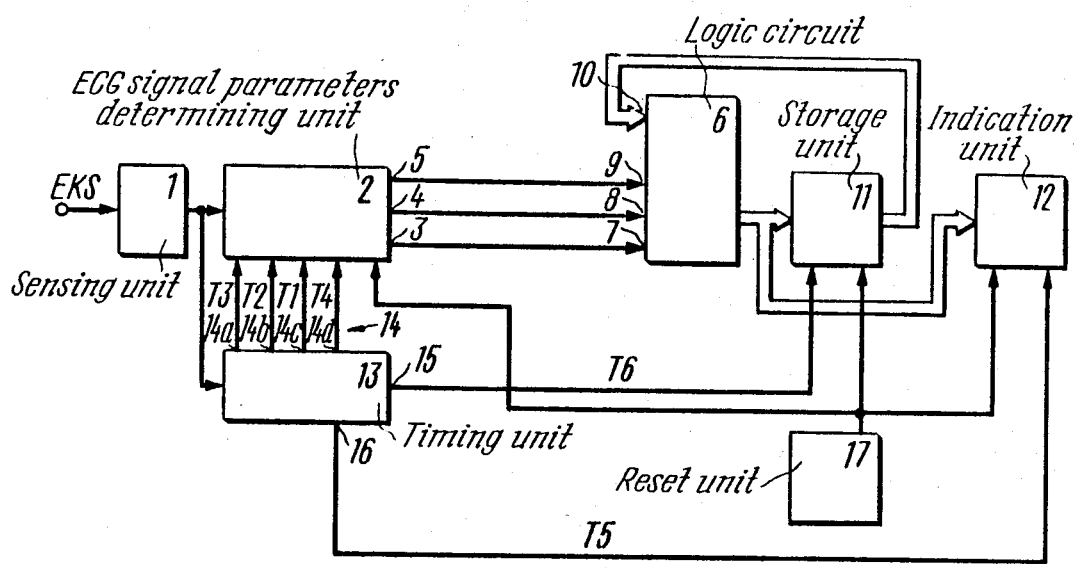
FIG. 1 is a block diagram of a heart monitoring device, according to one embodiment of the invention.

The heart monitoring device for monitoring the heart activity of a person by using an ECG signal comprises a sensing unit 1 (FIG. 1) arranged to detect R-waves of the ECG signal and having an input and an output, an ECG signal parameters determining unit 2 having a data input, a plurality of control inputs, a reset input and outputs 3, 4 and 5, a logic circuit 6 having inputs 7, 8, 9, a plurality of inputs 10 and a plurality of outputs, a storage unit 11 having a plurality of data inputs, a control input, a reset input and a plurality of outputs, an indication unit 12 having a plurality of data inputs, a control input and a reset input, a timing unit 13 having an input, a plurality of outputs 14 and outputs 15 and 16, and a reset unit 17 having an output.

The output of the sensing unit 1 is connected to a transducer (not shown), which can be provided with electrodes to pick up the ECG signal from a person. The output of the sensing unit 1 is connected to the data input of the ECG signal parameters determining unit 2 and to the input of the timing unit 13. The control inputs of the ECG signal parameters determining unit 2 are respectively connected to corresponding outputs of the plurality of outputs 14 of the timing unit 13. The reset input of the ECG signal parameters determining unit 2 is connected to the output of the reset unit 17. The output 3 of the ECG signal parameters determining unit 2 is connected to the input 7 of the logic circuit 6. The output 4 of the ECG signal determining unit 2 is connected to the input 8 of the logic circuit 6. The output 5 of the ECG signal determining unit 2 is connected to the input 9 of the logic circuit 6. The outputs of the logic circuit 6 are respectively connected to corresponding data inputs of the storage unit 11 and to corresponding data inputs of the indication unit 12. The outputs of the storage unit 11 are respectively connected to corresponding inputs of the plurality of inputs 10 of the logic circuit 6. The control input of the storage unit 11 is connected to the output 15 of the timing unit 13. The reset input of the storage unit 11 is connected to the output of the reset unit 17.

The control input of the indication unit 12 is connected to the output 16 of the timing unit 13. The reset input of the indication unit 12 is connected to the output of the reset unit 17.

Figure 2:
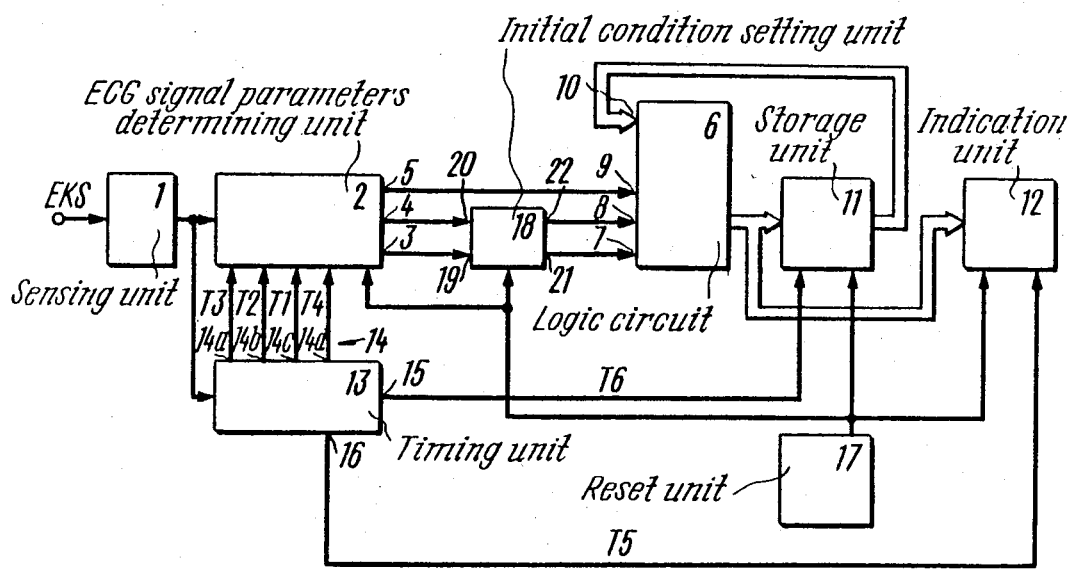
FIG. 2 is a block diagram of a heart monitoring device, according to another embodiment of the invention.

FIG. 2 is a block diagram of a heart monitoring device, which is provided with an initial condition setting unit 18 to prevent erroneous operation of the device in the beginning of analysis of the ECG signal. The initial condition setting unit 18 has data inputs 19 and 20, a reset input, and outputs 21 and 22. The output 3 of the ECG signal parameters determining unit 2 is connected to the data input 19 of the initial condition setting unit 18. The output 4 of the ECG signal parameters determining unit 2 is connected to the data input 20 of the initial condition setting unit 18. The output 21 of the initial condition setting unit 18 is connected to the input 7 of the logic circuit 6. The output 22 of the initial condition setting unit 18 is connected to the input 8 of the logic circuit 6. The reset input of the initial condition setting unit 18 is connected to the output of the reset unit 17.

The ECG signal parameters determining unit 2 comprises a pulse oscillator 23 (FIG. 3), a frequency divider 24 having a division ratio of five, counters 25, 26 and 27, a reversible counter 28, registers 29, 30 and 31, a shift register 32, bus drivers 33, 34, 35, 36, 37 and 38, a comparator 41, and flip-flops 42, 43 and 44.

The input of the pulse oscillator 23 constitutes the input of the ECG signal parameters determining unit 2 and is connected to the output of the sensing unit 1. The output of the oscillator 23 is connected to the input of the frequency divider 24, to the counting input of the counter 26, to the counting input of the counter 27 and to the down-counting input of the reversible counter 28. The output of the frequency divider 24 is connected to the counting input of the counter 25. The reset inputs of the counters 25, 26 and 27 are connected to the output 14a of the plurality of outputs 14 of the timing unit 13.

The control input of the reversible counter 28 is connected to the output 14b of the plurality of outputs 14 of the timing unit 13.

The outputs of the counter 25 are respectively connected to corresponding data inputs of the register 29. The outputs of the counter 26 are respectively connected to corresponding data inputs of the register 30. The outputs of the counter 27 are respectively connected to corresponding data inputs of the shift register 32 and to corresponding data inputs of the reversible counter 28. The outputs of the reversible counter 28 are respectively connected to corresponding data inputs of the register 31. The control inputs of the registers 29, 30 and 31 and the control input of the shift register 32 are connected to the output 14c of the plurality of outputs 14 of the timing unit 13.

The outputs of the register 29 are respectively connected to corresponding data inputs of the bus driver 33.

The outputs of the register 30 are respectively connected to corresponding data inputs of the bus driver 34.

The outputs of a first plurality of outputs of the shift register 32 are respectively connected to corresponding data inputs of the bus driver 35.

The outputs of a second plurality of outputs of the shift register 32 are respectively connected to corresponding data inputs of the bus driver 36.

The outputs of a third plurality of outputs of the shift register 32 are respectively connected to corresponding data inputs of the bus driver 37.

The outputs of the register 31 are respectively connected to corresponding data inputs of the bus driver 38.

The control inputs of the bus drivers 33 and 38 are connected to the output 14b of the timing unit 13.

The control inputs of the bus drivers 35 and 36 are connected to the output 14a of the timing unit 13.

The control inputs of the bus drivers 34 and 37 are connected to the output 14d of the plurality of outputs 14 of the timing unit 13.

The outputs of the bus drivers 33, 34 and 35 form a common bus 39. The outputs of the bus drivers 36, 37 and 38 form a common bus 40.

The lines of the bus 39 are respectively connected to corresponding inputs of a first plurality of data inputs of the comparator 41. The lines of the bus 40 are respectively connected to corresponding inputs of a second plurality of data inputs of the comparator 41.

The output of the comparator 41 is connected to the data inputs of the flip-flops 42, 43 and 44. The clock input of the flip-flop 42 is connected to the output 14b of the timing unit 13. The clock input of the flip-flop 43 is connected to the output 14a of the timing unit 13. The clock input of the flip-flop 44 is connected to the output 14d of the timing unit 13.

The direct output of the flip-flop 42 constitutes the output 3 of the ECG signal parameters determining unit 2. The inverted output of the flip-flop 43 constitutes the output 4 of the ECG signal parameters determining unit 2. The inverted output of the flip-flop 44 constitutes the output 5 of the ECG signal parameters determining unit 2.

The logic circuit 6 (FIG. 4) comprises AND gates 45, 46, 47, 48, 49, 50, 51, 52, 53, 54, 55, 56, 57, 58, 59, 60, 61, 62 and 63, OR gates 64, 65, 66 and 67, and a NOT gate 68. The storage unit 11 (FIG. 5) comprises OR gates 69 and 70, flip-flops 71, 72, 73, 74 and 75. The indication unit 12 (FIG. 6) comprises AND gates 76, 77, 78, 79, 80 and 81, counters 82, 83, 84, 85 and 86, indicator control units 87, 88, 89, 90, 91 and 92, and indicators 93, 94, 95, 96, 97 and 98.

The elements of the logic circuit 6 are connected as follows.

A first input of the AND gate 45 (FIG. 4), a first input of the AND gate 46 and the input of the NOT gate 68 are connected with each other forming the input 7 of the logic circuit 6.

A second input of the AND gate 45 and a second (inverting) input of the AND gate 46 are connected to each other forming the input 8 of the logic circuit 6.

The output of the AND gate 45 is connected to a first input of the AND gate 50, to a first input of the AND gate 53, to a first input of the AND gate 54, to a first input of the AND gate 55 and to a first input of the AND gate 59.

The output of the AND gate 46 is connected to a first input of AND gate 48, to a first input of the AND gate 51, to a first input of the AND gate 52, to a first input of the AND gate 57 and to a first input of the AND gate 60.

The output of the NOT gate 68 is connected to a first input of the AND gate 49, to a first input of the AND gate 56, to a first input of the AND gate 58, to a first input of the AND gate 61 and to a first input of the AND gate 47.

Second inputs of the AND gates 48, 49 and 50 are connected to the output of the flip-flop 71 (FIG. 5) of the storage unit 11.

Second inputs of the AND gates 51, 58 and 59 (FIG. 4) are connected to the output of the flip-flop 72 (FIG. 5) of the storage unit 11.

Second inputs of the AND gates 52, 54 and 47 (FIG. 4) are connected to the output of the flip-flop 75 (FIG. 5) of the storage unit 11.

Second inputs of the AND gates 53, 60 and 61 (FIG. 4) are connected to the output of the flip-flop 74 (FIG. 5) of the storage unit 11.

Second inputs of the AND gates 55, 56 and 57 (FIG. 4) are connected to the output of the flip-flop 73 (FIG. 5) of the storage unit 11.

The output of the AND gate 48 (FIG. 4) is connected to a first input of the OR gate 67. The output of the AND gate 49 is connected to a second input of the OR gate 67.

The AND gate 62 has an inverting input connected to a first input of the AND gate 63. These interconnected inputs of the AND gates 62 and 63 form the input 9 of the logic circuit 6. Second inputs of the AND gates 62 and 63 are connected to the output of the AND gate 51. The output of the AND gate 63 is connected to a first input of the OR gate 66.

The output of the AND gate 53 is connected to a first input of the OR gate 64. The output of the AND gate 54 is connected to a second input of the OR gate 64.

The output of the AND gate 55 is connected to a first input of the OR gate 65. The output of the AND gate 56 is connected to a second input of the OR gate 65.

The output of the AND gate 58 is connected to a second input of the OR gate 66. The output of the AND gate 59 is connected to a third input of the OR gate 66. The output of the AND gate 60 is connected to a fourth input of the OR gate 66. The output of the AND gate 61 is connected to a fifth input of the OR gate 66. The output of the AND gate 47 is connected to a sixth input of the OR gate 66.

The elements of the storage unit 11 are connected as follows.

A first input of the OR gate 69 (FIG. 5) is connected to the output of the OR gate 67 (FIG. 4) of the logic circuit 6. A second input of the OR gate 69 (FIG. 5) is connected to the output of the AND gate 52 (FIG. 4) of the logic circuit 6. A third input of the OR gate 69 (FIG. 5) is connected to the output of the AND gate 62 (FIG. 4) of the logic circuit 6. The output of the OR gate 69 (FIG. 5) is connected to the data input of the flip-flop 71. The data input of the flip-flop 72 is connected to the output of the AND gate 50 (FIG. 4) of the logic circuit 6. A first input of the OR gate 70 (FIG. 5) is connected to the output of the OR gate 64 (FIG. 4) of the logic circuit 6. A second input of the OR gate 70 (FIG. 5) is connected to the output of the OR gate 65 (FIG. 4) of the logic circuit 6. The output of the OR gate 70 is connected to the data input of the flip-flop 73.

The data input of the flip-flop 74 (FIG. 5) is connected to the output of the AND gate 57 (FIG. 4) of the logic circuit 6.

The data input of the flip-flop 75 (FIG. 5) is connected to the output of the OR gate 66 (FIG. 4) of the logic circuit 6.

The clock inputs of the flip-flops 71, 72, 73, 74 and 75 (FIG. 5) are connected to the output 15 of the timing unit 13 (FIG. 1).

The reset inputs of the flip-flops 71, 72, 73 and 74 and the set input of the flip-flop 75 are connected to the output of the reset unit 17 (FIG. 1).

The elements of the indication unit 12 are connected as follows.

A first input of the AND gate 76 (FIG. 6) is connected to the output of the OR gate 66 (FIG. 4) of the logic circuit 6.

A first input of the OR gate 77 (FIG. 5) is connected to the output of the OR gate 67 (FIG. 4) of the logic circuit 6.

A first input of the AND gate 78 (FIG. 6) is connected to the output of the AND gate 52 (FIG. 4) of the logic circuit 6.

A first input of the AND gate 79 (FIG. 6) is connected to the output of the OR gate 64 (FIG. 4) of the logic circuit 6.

A first input of the AND gate 80 (FIG. 6) is connected to the output of the OR gate 65 (FIG. 4) of the logic circuit 6.

A first input of the AND gate 81 (FIG. 6) is connected to the output of the AND gate 62 (FIG. 4) of the logic circuit 6.

Second inputs of the AND gates 76, 77, 78, 79, 80 and 81 (FIG. 6) are connected to the output 16 of the timing unit 13 (FIG. 1).

The output of the AND gate 76 (FIG. 6) is connected to the input of the indicator control unit 87 whose output is connected to the input of the indicator 93.

The outputs of the AND gates 77, 78, 79, 80 and 81 are respectively connected to the counting inputs of the counters 82, 83, 84, 85 and 86.

The outputs of the counter 82 are respectively connected to the inputs of the indicator control unit 88, the outputs of which are respectively connected to the inputs of the indicator 94. The outputs of the counter 83 are respectively connected to the inputs of the indicator control unit 89, the outputs of which are respectively connected to the inputs of the indicator 95. The outputs of the counter 84 are respectively connected to the inputs of the indicator control unit 90, the outputs of which are respectively connected to the inputs of the indicator 96. The outputs of the counter 85 are respectively connected to the inputs of the indicator control unit 91, the outputs of which are respectively connected to the inputs of the indicator 97. The outputs of the counter 86 are respectively connected to the inputs of the indicator control unit 92, the outputs of which are respectively connected to the inputs of the indicator 98.

The reset inputs of the counters 82, 83, 84, 85 and 86 are connected to the output of the reset unit 17 (FIG. 1).

The indicator 93 (FIG. 6) indicates a normal rhythm, the indicator 94 indicates the number of grouped, extrasystoles, the indicator 95 indicates the number of single extrasystoles, the indicator 96 indicates the number of blocks, the indicator 97 indicates the number of dangerous blocks, and the indicator 98 indicates the number of bigeminal extrasystoles.

The initial condition setting unit 18 (FIG. 7) comprises a double-pole three-position switch 99, Exclusive OR gates 100 and 101, and NOR gate 102, a NOT gate 103, an OR gate 104, AND gates 105 and 106, and a flip-flop 107. A first input of the AND gate 105 and a first input of the Exclusive OR gate 100 are connected to each other forming the input 19 of the initial condition setting unit 18. A first input of the AND gate 106 and a first input of the Exclusive OR gate 101 are connected to each other forming the input 20 of the initial condition setting unit 18.

When the switch 99 is set to a first position, it connects a source E of a signal of logic one to a second input of the Exclusive OR gate 100 and to a second input of the Exclusive OR gate 101. In its second position the switch 99 connects the second input of the Exclusive OR gate 100 to the source E and the second input of the Exclusive OR gate 101 to ground. In its third position the switch 99 connects the second input of the Exclusive OR gate 100 and the second input of the Exclusive OR gate 101 to ground. The outputs of the Exclusive OR gates 100 and 101 are respectively connected to the inputs of the NOR gate 102. The output of the NOR gate 102 is connected to a first input of the OR gate 104. The second input of the Exclusive OR gate 100 is connected to the switch 99 and to the input of the NOT gate 103. The output of the NOT gate 103 is connected to a second input of the OR gate 104. The output of the OR gate 104 is connected to a second input of the AND gate 105, to a second input of the AND gate 106 and to the set input of the flip-flop 107.

The reset input of the flip-flop 107 is connected to the output of the reset unit 17 (FIG. 1). The output of the flip-flop 107 (FIG. 7) is connected to a third input of the OR gate 104.

The output of the AND gate 105 constitutes the output 21 of the initial condition setting unit 18. The output of the AND gate 106 constitutes the output 22 of the initial condition setting unit 18.

Figure 8:
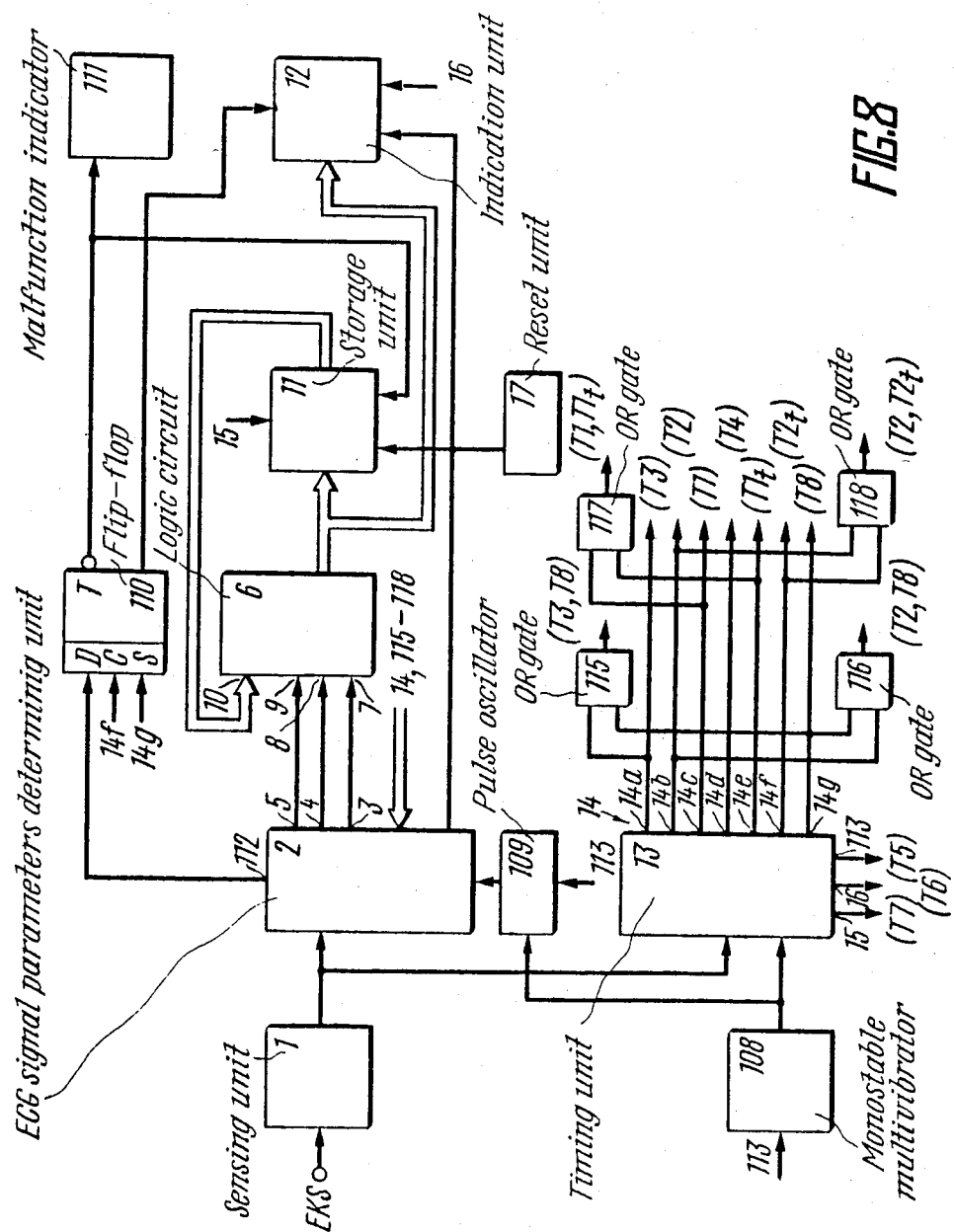
FIG. 8 is a block diagram of a heart monitoring device, according to still another embodiment of the invention.

FIG. 8 is a block diagram of a heart monitoring device, which, to ensure a more reliable diagnosis of arrhythmia, further comprises a monostable multivibrator 108, a pulse oscillator 109 having an enable input, a disable input and an output, a flip-flop 110, and a malfunction indicator 111. The ECG signal parameters determining unit 2 is further provided with a second data input and a fourth output 112. The timing unit 13 is further provided with a second input and an additional output 113. The plurality of outputs 14 includes outputs 14a, 14b, 14c, 14d, 14e, 14f and 14g. The storage unit 11 is further provided with a second reset input, and the indication unit 12 is further provided with an indication permitting input.

The enable input of the monostable multivibrator 108 is connected to the output 113 of the timing unit 13. The output of the multivibrator 108 is connected to the second input of the timing unit 13 and to the disable input of the pulse oscillator 109. The enable input of the pulse oscillator 109 is connected to the output 113 of the timing unit 13, and the output of the pulse oscillator 109 is connected to the second input of the ECG signal parameters determining unit 2. The data input of the flip-flop 110 is connected to the output 112 of the ECG signal parameters determining unit 2. The clock input and the reset input of the flip-flop 110 are respectively connected to the outputs 14f and 14g of the timing unit 13. The inverted output of the flip-flop 110 is connected to the input of the malfunction indicator 111 and to the second reset input of the storage unit 11. The direct output of the flip-flop 110 is connected to the indication permitting input of the indication unit 12.

In this case the ECG signal parameters determining unit 2 (FIG. 3) further comprises a register 114 providing intermediate storage of the duration of an RR interval. The data inputs of the register 114 are respectively connected to the outputs of the counter 27. The control input of the register 114 is connected to the output 14b of the timing unit 13. The outputs of the register 114 are respectively connected to the data inputs of the reversible counter 28.

The reset input of each of the counters 25, 26 and 27 is connected to the outputs 14a and 14g of the timing unit 13 through an OR gate 115 (FIG. 8). The control input of the reversible counter 28 (FIG. 3) is connected to the outputs 14b and 14g of the timing unit 13 through an OR gate 116 (FIG. 8). The control input of each of the registers 29 and 31 (FIG. 3) is connected to the outputs 14c and 14e of the timing unit 13 through an OR gate 117 (FIG. 8). The control input of each of the bus drivers 33 and 38 (FIG. 3) is connected to the outputs 14b and 14f of the timing unit 13 through an OR gate 118 (FIG. 8).

The input of the frequency divider 24 (FIG. 3), the counting inputs of the counters 26 and 27 and the down-counting input of the reversible counter 28 are connected to the output of an OR gate 119 having a first input connected to the output of the pulse oscillator 23 and a second input connected to the output of the pulse oscillator 109 in the ECG signal parameters determining unit 2.

The storage unit 11 (FIG. 5) further comprises an OR gate 120 having its output connected to the reset inputs of the flip-flops 71, 72, 73 and 74 and to the set input of the flip-flop 75. The OR gate 120 has a first input connected to the output of the reset unit 17 and a second input connected to the direct output of the flip-flop 110. The inputs of the OR gate 120 constitute the reset inputs of the storage unit 11. Each of the AND gates 76, 77, 78, 79, 80 and 81 in the indication unit 12 (FIG. 6) has a third input connected to the inverted output of the flip-flop 110.

The heart monitoring device operates as follows.

The ECG signal (FIG. 9a) is obtained, e.g. by means of electrodes, from the person being examined and is supplied to the input of the sensing unit 1, which produces a synchronizing pulse S (FIG. 9b) in response to each R-wave of the ECG signal. The time intervals between the synchronizing pulses S correspond to the RR intervals of the ECG signal: $RR_{i-1}$, $RR_i$, and so on. The synchronizing pulses S are applied to the data input of the ECG signal parameters determining unit 2 (FIG. 1) and to the input of the timing unit 13.

Figure 3:
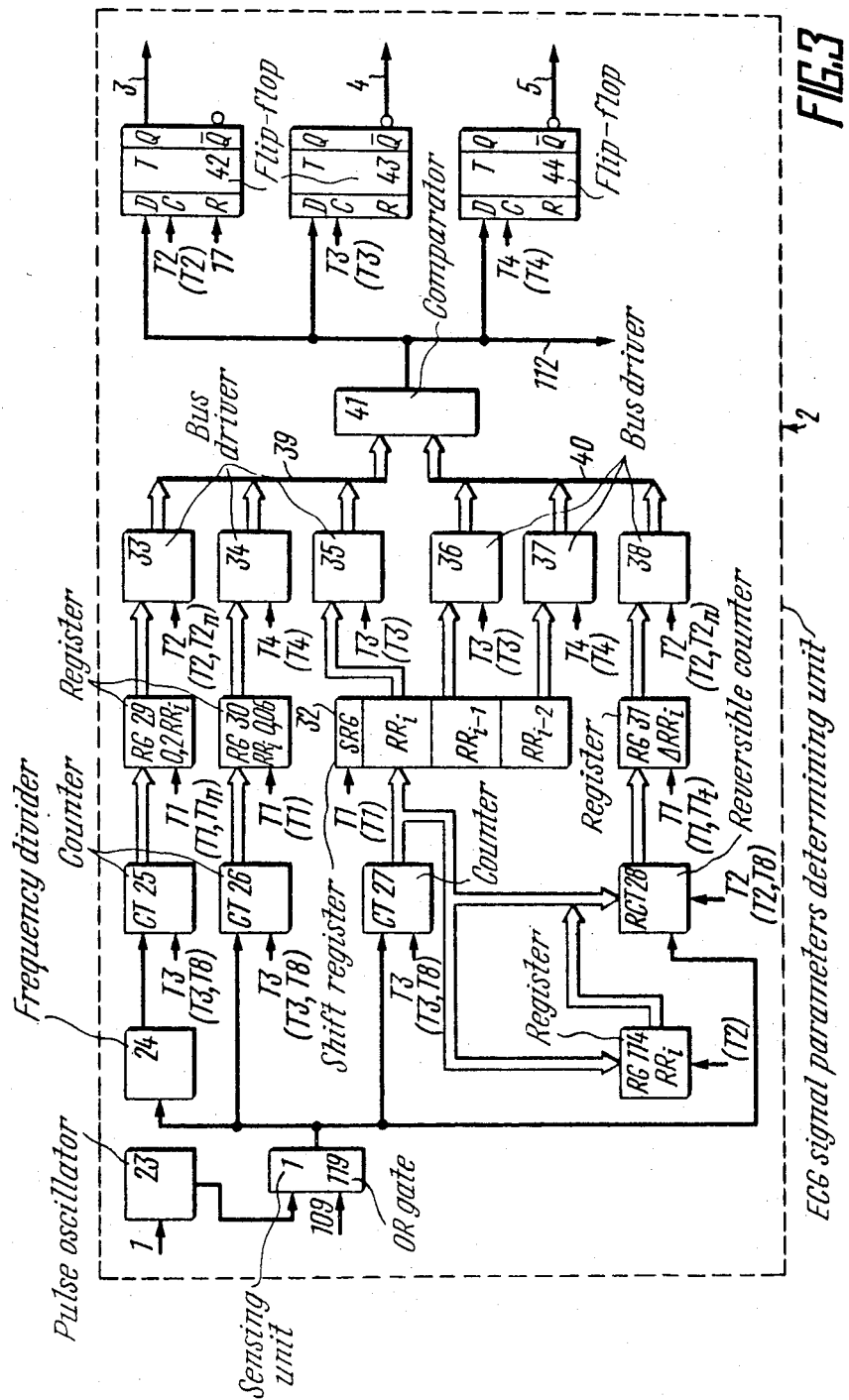
FIG. 3 is a block diagram of the ECG signal parameters determining unit, according to the preferred embodiment of the invention.

Each synchronizing pulse S (FIG. 9b) starts the pulse oscillator 23 (FIG. 3). The oscillator 23 develops clock pulses C (FIG. 8c), which are used for measurement of the time parameters of the ECG signal.

In the interval between the first and second clock pulses of each cycle of analysis of the ECG signal the timing unit 13 generates commands $T_1$, $T_2$, $T_3$, $T_4$, $T_5$ and $T_6$ (FIG. 9d), which control the device operation. The commands supplied from the timing unit 13 to units of the device in which the circuits providing check on the device operation (i.e. the monostable multivibrator 108, the pulse oscillator 109, the flip-flop 110 and the malfunction indicator 111) are not used, are shown in the drawings without brackets.

During each cycle of analysis of the ECG signal the counter 25 (FIG. 3) in the ECG signal parameters determining unit 2 counts the number of clock pulses passing through the frequency divider 24, which has a division ratio of five. Therefore, when a synchronizing pulse S is developed, the counter 25 has a count corresponding to the time period $0.2RR_i$. The counter 26, which starts with a count corresponding, for example, to $-0.06$ s, reaches a count corresponding to the time period of $(RR_i-0.06 \text{ s})$.

The counter 27 reaches a count corresponding to the duration of the time interval $RR_{i-1}$.

Upon termination of the preceding cycle of analysis, the reversible counter 28 is stored with a value corresponding to the duration of the time interval $RR_{i-1}$. During the next cycle of analysis clock pulses are successively subtracted from the contents of the reversible counter 28, with the result that the counter 28 goes to a count corresponding to the time period of $\Delta RR_i = RR_i - RR_{i-1}$. On application of the command $T_1$ generated by the timing unit 13, the data from the counters 25, 26, 27 and 28 are respectively transferred to the registers 29, 30, 32 and 31.

As this takes place, the shift register 32 continues to hold values corresponding to the durations of the preceding intervals $RR_{i-1}$ and $RR_{i-2}$.

On application of the command $T_2$, the following operations are performed:
the reversible counter 28 is stored with data from the counter 27;
the comparator 41 compares the values of $0.2RR_i$ and $\Delta RR_i$ respectively supplied from the registers 29 and 31 through the bus drivers 33 and 38 to the buses 39 and 40;

the flip-flop 42 is stored with the result of comparison between the values of $0.2RR_i$ and $\Delta RR_i$. If $$1\Delta RR_i < 0.2RR_i, \quad (3)$$

the flip-flop 42 is set to a state of logic zero. If $$\Delta RR_i \geq 0.2RR_i, \quad (4)$$

the flip-flop 42 is set to a state of logic one. The result of comparison is derived from the output 3 of the flip-flop 42.

On application of the command $T_3$, the following operations are performed:
the counters 25, 26 and 27 are reset to their initial states (to zero in the case of the counters 25 and 27, and to a state corresponding to $-0.06$ s in the case of the counter 26);
the comparator 41 compares the values of $RR_i$ and $RR_{i-1}$ respectively supplied from the outputs of the shift register 32 through the bus drivers 35 and 36 to the buses 39 and 40;
the flip-flop 43 is stored with the result of comparison between the values of $RR_i$ and $RR_{i-1}$. If $$RR_i < RR_{i-1}, \quad (5)$$

the flip-flop 43 is set to a state of logic one. If $$RR_i \geq RR_{i-1}, \quad (6)$$

the flip-flop 43 is set to a state of logic yero. The result of comparison is derived from the inverted output 4 of the flip-flop 43.

On application of the command $T_4$, the following operations are performed:
the comparator 41 compares the values of $(RR_i-0.06 \text{ s})$ and $RR_{i-2}$ respectively supplied from the outputs of the register 30 and the shift register 32 through the bus drivers 34 and 37 to the buses 39 and 40;
the flip-flop 44 is stored with the result of comparison between the values of $(RR_i-0.06 \text{ s})$ and $RR_{i-2}$. If $$RR_i - RR_{i-2} < 0.06 \text{ s}, \quad (7)$$

the flip-flop 44 is set to a state of logic one. If $$RR_i - RR_{i-2} \geq 0.06 \text{ s}, \quad (8)$$

the flip-flop 44 is set to a state of logic zero. The result of comparison is derived from the inverted output 5 of the flip-flop 44.

In the logic circuit 6 (FIG. 4) the data supplied to the inputs 7, 8 and 9 from the outputs 3, 4 and 5, respectively, of the ECG signal parameters determining unit 2 (FIG. 1) are combined as follows.

If the inequalities (4) and (6) are satisfied, the AND gate 45 (FIG. 6) operates supplying a signal of logic one to the line "+". If the inequalities (4) and (5) are satisfied, the AND gate 46 operates supplying a signal of logic one to the line "−". If the inequality (3) is satisfied, the NOT gate 68 supplies a signal of logic one to the line "∅".

The subsequent process of analysis of the available data, which process provides the detection, count and indication of irregularities in the cardiac rhythm, is illustrated by the table shown in FIG. 10. The contents of the table squares correspond to the detected types of cardiac rhythm. The following abbreviations are assumed:

N=normal cardiac rhythm,
E=single extrasystole,
GE=grouped extrasystoles,
B=block,
DB=dangerous block,
Big=bigeminy.

These symbols in the table are connected by arrows to the numbers of those flip-flops in the storage unit 11 which are set to states of logic one upon detection of corresponding types of cardiac rhythm.

When the heart monitoring device is turned on, the reset unit 17 (FIG. 1) develops a reset signal, which is supplied, for at least three consecutive RR intervals, to the reset input of the flip-flop 42 (FIG. 3) of the ECG signal parameters determining unit 2, to the reset inputs of the flip-flops 71, 72, 73 and 74 (FIG. 5), to the set input of the flip-flop 75 of the storage unit 11 and to the reset inputs of the counters 82, 83, 84, 85 and 86 (FIG. 6) of the indication unit 12.

During the time of application of the reset signal, constituting, for example, 10 seconds, the ECG signal parameters determining unit 2 (FIG. 1) accumulates data on three consecutive RR intervals of the ECG signal, the line "∅" in the logic circuit 6 (FIG. 4) is supplied with a signal of logic one, and the flip-flop 75 (FIG. 5) in the storage unit 11 is maintained in the logic one state. The AND gate 47 (FIG. 4) and the OR gate 66 develop signals of logic one, and, on application of the commands T$_5$ from the output 16 of the timing unit 13 (FIG. 1), the indicator control unit 87 is supplied through the AND gate 76 (FIG. 6) of the indication unit 12 with a signal of logic one, with the result that the indicator 93 indicates a normal cardiac rhythm.

In this case the presence of a signal of logic one at the output of the OR gate 66 corresponds to a "seventh" combination of signals at the outputs of the logic circuit 6.

Figure 4:
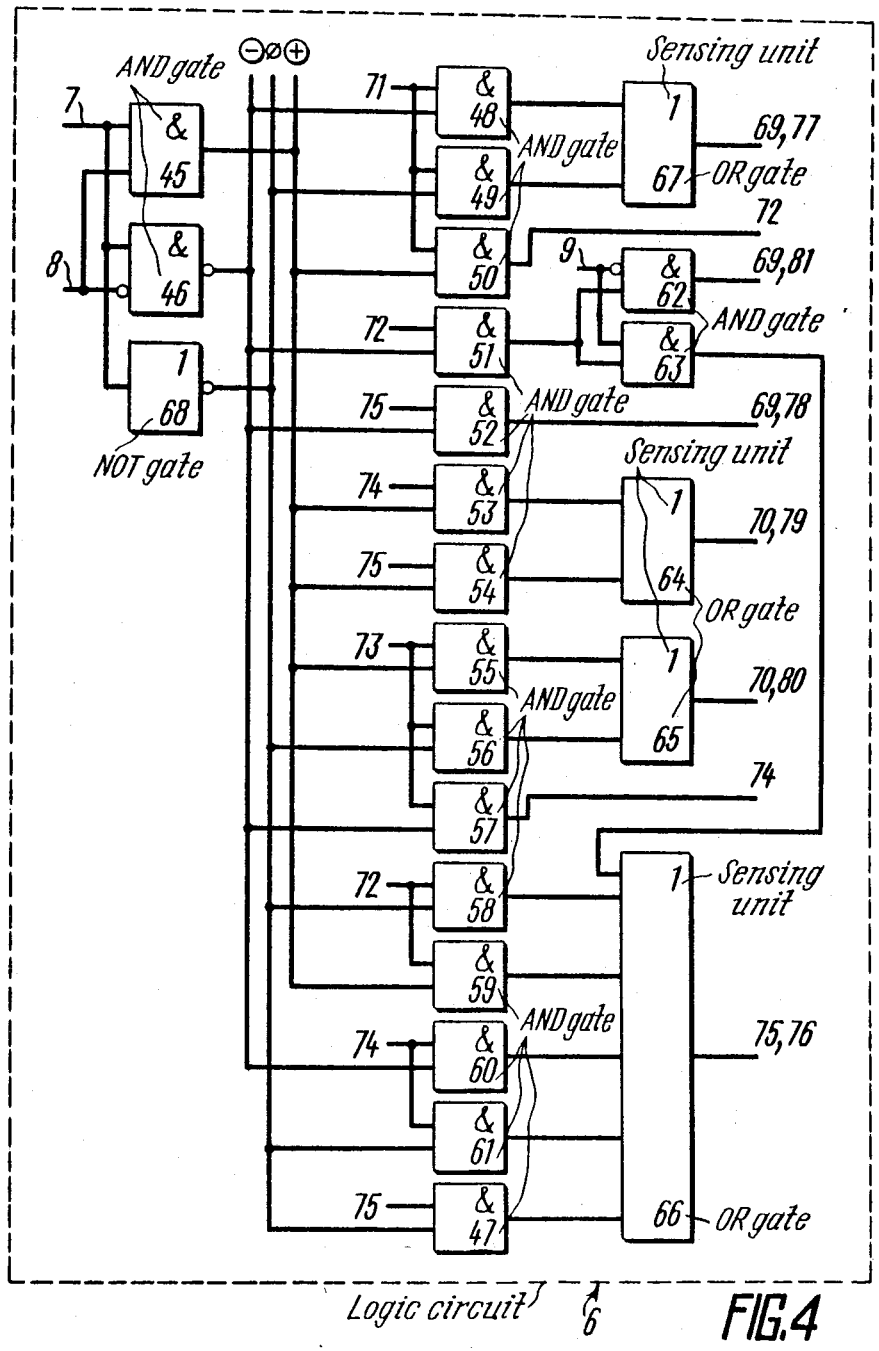
FIG. 4 is a block diagram of the logic circuit, according to the preferred embodiment of the invention.

The presence of a signal of logic one at the output of the flip-flop 75 (FIG. 5) in the storage unit 11 means that the storage unit 11 is stored with a code corresponding to the seventh combination of signals at the outputs of the logic circuit 6 (FIG. 4).

In addition, the signal of logic one from the output of the OR gate 66, upon application of the command T$_6$ from the output 15 of the timing unit 13, will set the flip-flop 75 (FIG. 5) of the storage unit 11 to a logic one state, each time preparing thereby the storage unit 11 to the next cycle of analysis of cardiac rhythm.

The described state corresponds to the square E2 in the table of FIG. 10. Thus, after termination of the reset signal, the heart monitoring device will contain accumulated data on the relation between the durations of three consecutive RR intervals of the ECG signal and will analyse this data in reference to the normal cardiac rhythm occurring before the analysed intervals.

Figure 11A:
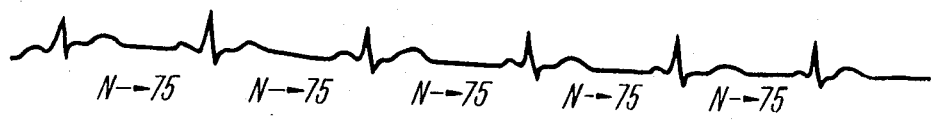
FIGS. 11a–11f are exemplary timing diagrams of electrocardiograph (ECG) signals.

If the person being examined has a normal cardiac rhythm (FIG. 11a), the operations described above are performed after the appearance of each R-wave upon application of the commands T$_1$, T$_2$, T$_3$, T$_4$, T$_5$, and T$_6$. As this takes place, the inequality (3) is satisfied so that the flip-flop 42 (FIG. 3) is set to a state of logic zero, the line "∅" of the logic circuit 6 (FIG. 4) is energized, and the AND gate 47 (FIG. 6), the OR gate 66, the AND gate 76, the indicator control unit 87 and the indicator 93 are operated, with the result that the indicator 93 indicates a normal cardiac rhythm. In the storage unit 11 (FIG. 5) the flip-flop 75 is set to a state of logic one.

Figure 11B:
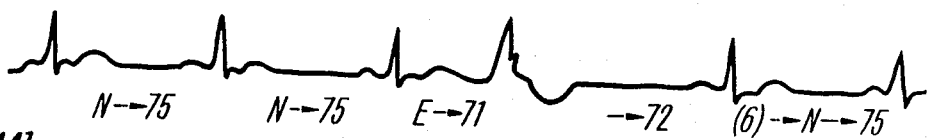

When a single extrasystole (FIG. 11b) appears against the background of a normal cardiac rhythm, the inequalities (4) and (5) are satisfied and each of the flip-flops 42 and 43 (FIG. 3) in the ECG signal parameters determining unit 2 is stored with a logic one. In this case the line "−" of the logic circuit 6 (FIG. 4) is energized. Since the output of the flip-flop 75 (FIG. 5) remains logic one, the AND gates 52 (FIG. 4) and 78 (FIG. 6) are operated, the counter 83 increases its count by one and the indicator 95, operated by the indicator control unit 89, indicates in decimal code the number of single extrasystoles. Through the OR gate 69 (FIG. 5) the flip-flop 71 is set to a logic one state.

In this case the presence of a signal of logic one at the output of the AND gate 52 (FIG. 4) corresponds to a "third" combination of signals at the outputs of the logic circuit 6. The appearance of a signal of logic one at the output of the flip-flop 71 (FIG. 5) means that the storage unit 11 is stored with a code corresponding to the third combination of signals at the outputs of the logic circuit 6. This state corresponds to the square E1 in the table shown in FIG. 10.

When an extrasystole is followed by a compensatory pause (FIG. 11b), the inequalities (4) and (6) are satisfied. The flip-flop 42 (FIG. 3) is set to a logic one state and the flip-flop 43 is set to a logic zero state. The line "+" of the logic circuit 6 (FIG. 4) is energized, and the AND gate 50 is operated, which corresponds to the establishment of a "second" combination of signals at the outputs of the logic circuit 6. The flip-flop 72 (FIG. 5) is stored with a logic one.

Figure 11C:
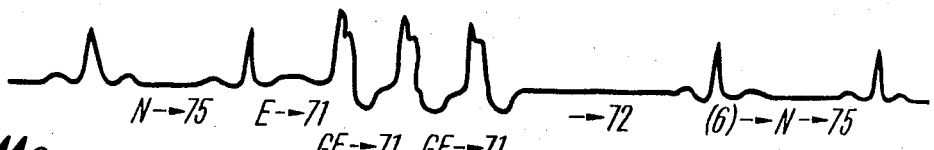
Figure 11D:
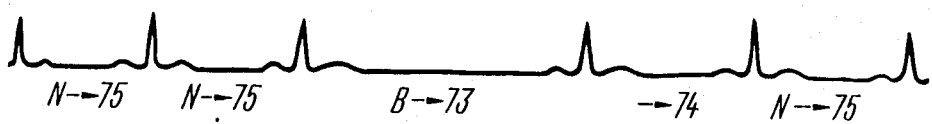
Figure 11E:
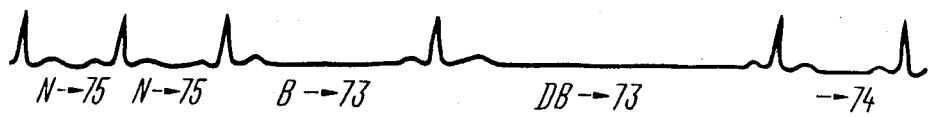
Figure 11F:

The presence of a signal of logic one at the output of the flip-flop 72 means that the storage unit 11 is stored with a code corresponding to the second combination of signals at the outputs of the logic gate 6 (FIG. 4). This state of the device corresponds to the square A3 of the table shown in FIG. 10 and represents an intermediate state, because in such an event the duration of one more RR interval must be analysed to distinguish a single extrasystole from bigeminy (FIG. 11f). In case of a normal interval which follows a compensatory pause (FIG. 11b), the inequalities (4), (5) and (8) are satisfied. In such a case the line "−" of the logic circuit 6 (FIG. 4) is energized. Through the AND gates 51 and 63 (FIG. 6), the OR gate 66 and the AND gate 76 (FIG. 6) the indicator control unit 87 is supplied with a signal of logic one, with the result that the indicator 93 indicates a normal cardiac rhythm.

In the storage unit 11 (FIG. 5) the flip-flop 75 is set to a state of logic one, which corresponds to the lower line of the square B1 in the table of FIG. 10.

When bigeminy (FIG. 11f) appears against the background of a normal rhythm (FIG. 11a), the first extrasystolic heart contraction is diagnosed as a single extrasystole (see the square E1 in the table of FIG. 10). Upon appearance of an elongated RR interval (FIG. 11f) following the extrasystole, the device passes to an intermediate state (the square A3 in the table of FIG. 10). Then, upon appearance of the second extrasystolic heart contraction (FIG. 11f), the inequalities (4), (5) and (7) are satisfied. The signal at the line "−" of the logic circuit 6 (FIG. 4) becomes a logic one. Through the AND gates 51, 62 (FIG. 4) and 81 (FIG. 6) the counter 86 increases its count by one. The indicator control unit 92 operates the indicator 98, which indicates in decimal code the number of bigeminal extrasystoles. The signal of logic one from the output of the AND gate 62 (FIG. 4) of the logic circuit 6 passes through the OR gate 69 (FIG. 5) of the storage unit 11 and sets the flip-flop 71 in a logic one state (see the upper line in the square B1, FIG. 10).

In this case the presence of a signal of logic one at the output of the AND gate 62 (FIG. 4) corresponds to an "eighth" combination of signals at the outputs of the logic gate 6, while the appearance of a signal of logic one at the output of the flip-flop 71 (FIG. 5) means that the storage unit 11 is stored with a code corresponding to the eighth combination of signals at the outputs of the logic circuit 6. This code is the same as the code corresponding to the third combination of signals at the outputs of the logic circuit 6.

The subsequent diagnostic process under bigeminy conditions is conducted in the same way, as illustrated by the squares A3 and B1 (the upper line) in the table of FIG. 10.

In case of appearance of grouped extrasystoles (FIG. 11c), the first extrasystole is diagnosed as a single extrasystole (the square E1 in the table of FIG. 10). With the appearance of the second and subsequent extrasystoles (FIG. 11c), the inequality (3) is satisfied and the line "∅" of the logic circuit 6 (FIG. 4) is energized. Since the flip-flop 71 (FIG. 5) was set to a logic one state during the preceding cycle of analysis of cardiac rhythm, signals of logic one appear at the outputs of the AND gate 49 (FIG. 4) and the OR gate 67 of the logic circuit 6. Through the AND gate 77 (FIG. 6) the counter 82 increases its count by one. The indicator control unit 88 operates the indicator 94, which indicates in decimal code the number of grouped extrasystoles. The signal of logic one from the output of the OR gate 67 (FIG. 4) passes through the OR gate (FIG. 5) and is stored into the flip-flop 71. The diagnosis of such grouped extrasystoles is illustrated by the square A2 in the table of FIG. 10.

In this case the presence of a signal of logic one at the output of the OR gate 67 (FIG. 4) corresponds to a "first" combination of signals at the outputs of the logic circuit 6. The appearance of a signal of logic one at the output of the flip-flop 71 (FIG. 5) indicates that the storage unit 11 is stored with a code corresponding to the first combination of signals at the outputs of the logic circuit 6 and also to the eighth and third combination of signals at the outputs of the logic circuit 6 (FIG. 4). Transition to a normal rhythm is analysed in this case in the same way as the transition to a normal rhythm after a single extrasystole (see the square A3 and the lower line of the square B1 in the table of FIG. 10).

Group extrasystoles with successively shortening extrasystolic RR intervals are diagnosed in a similar way; the process of analysis in such a case is illustrated by the squares E1, A1, A3 and B1 (lower line) in the table of FIG. 10.

A block (a skipped heart beat, FIG. 11d) is diagnosed as follows. When an elongated RR interval appears against the background of a normal rhythm, the inequalities (4) and (6) are satisfied. In this case the line "+" of the logic circuit 6 (FIG. 4) becomes energized. Since the flip-flop 75 (FIG. 5) in the storage unit 11 was stored with a logic one during normal rhythm conditions, the AND gate 54 (FIG. 4), the OR gate 64 and the AND gate 79 (FIG. 6) are operated and the counter 84 increases its count by one. The indicator control unit 90 operates the indicator 96, which indicates in decimal code the number of blocks. In the storage unit 11 (FIG. 5) the flip-flop 73 is stored with a logic one, the signal of logic one being passed through the OR gate 70 (see the square E3 in the table of FIG. 10). The appearance of a signal of logic one at the output of the OR gate 64 (FIG. 4) corresponds to the establishment of a "fourth" combination of signals at the outputs of the logic circuit 6. The storage of this combination of signals in the storage unit 11 (FIG. 5) corresponds to the setting of the flip-flop 73 to a logic one state.

When an RR interval of normal length (FIG. 11d) follows a block, the inequalities (4) and (5) are satisfied and the line "−" of the logic circuit 6 (FIG. 4) becomes energized. The AND gate 57 operates establishing a "sixth" combination of signals at the outputs of the logic circuit 6, while the flip-flop 74 (FIG. 5) is set to a logic one state indicating that the storage unit 11 is stored with a code corresponding to the sixth combination of signals at the outputs of the logic circuit 6. This condition (see the square C1 in the table of FIG. 10) represents an intermediate state. To diagnose such a rhythm, it is necessary to have data on one more RR interval.

In case of appearance of a second consecutive normal RR interval (FIG. 11d), the inequality (3) is satisfied and the line "∅" is energized (FIG. 4). The AND gate 61 (FIG. 6), the OR gate 66 and the AND gate 76 (FIG. 6) are operated and the indicator control unit 87 operates the indicator 93, which indicates a normal cardiac rhythm. The flip-flop 75 (FIG. 5) is stored with a logic one. This condition corresponds to the square D2 in the table of FIG. 10.

In case of occurrence of dangerous blocks (FIG. 11e) characterized by successive lengthening of RR intervals, the first elongated interval is classified as a single block (see the square E3 in the table of FIG. 10). The lengthening of the following RR interval causes the inequalities (4) and (6) to be satisfied and the line "+" (FIG. 4) to become energized. Since the flip-flop 73 (FIG. 5) was set to a logic one state during the preceding cycle of analysis, the AND gate 55 (FIG. 4), the OR gate 65 and the AND gate 80 (FIG. 6) are operated and the counter 85 increases its count by one. The indicator control unit 91 operates the indicator 97, which indicates in decimal code the number of dangerous blocks. The flip-flop 73 (FIG. 5) is stored with a logic one through the OR gate 70. The described diagnostic process is illustrated by the square C3 in the table of FIG. 10.

In this case the presence of a signal of logic one at the output of the OR gate 65 (FIG. 4) corresponds to a "fifth" combination of signals at the outputs of the logic circuit 6. The setting of the flip-flop 73 (FIG. 5) to a logic one state indicates that the storage unit 11 is stored with a code corresponding to the fifth combination of signals at the outputs of the logic circuit 6. This code is the same as the code corresponding to the fourth combination of signals at the outputs of the logic circuit 6. The diagnosis of the transition to a normal rhythm is carried out in the same manner as in the case of a single block described above.

The number of actually possible combinations of durations of RR intervals analysed by the heart monitoring device is rather great. The examples described above are most typical and most often met. When other types of cardiac rhythm are diagnosed, the device operation may be analyzed by using the table of FIG. 10 and the accompanying drawings, as it was done in the examples considered above.

Thus, the heart monitoring device makes possible prolonged and continuous monitoring of various kinds of irregularities in the heart rate and cardiac rhythm of a person during treatment of cardiovascular deseases, preventive inspections, rehabilitation, tests under physical loads, and during extreme conditions.

The conclusion concerning cardiac rhythm is drawn by using a limited amount of data on the relative durations of no more than three consecutive RR intervals and the data on the cardiac rhythm obtained in the preceding cycle of analysis. By this means the amount of logical operations required for diagnosis is reduced and the implementation of the device is simplified.

As a result of monitoring of irregularities in the heart rate and cardiac rhythm, the device counts and indicates in decimal code the number of occurrences of each of the irregularities mentioned above.

The initial condition setting unit 18 is shown in more detail in FIG. 7. On turning on of the heart monitoring device, the reset unit 17 (FIG. 2) resets the flip-flop 107 (FIG. 7) to zero and causes the ECG signal parameters determining unit 2 (FIG. 2) to develop at its output 3 a signal of logic zero. Then, if the switch 99 (FIG. 7) is set to the first or second position, the second input of the Exclusive OR gate 100 and the input of the NOT gate 103 are supplied with signals of logic one, which do not coincide with the zero signal applied to the input 19 of the initial condition setting unit 18 (FIG. 2) and passed to the first input of the Exclusive OR gate 100 (FIG. 7). The appearance of a signal of logic one at the output of the Exclusive OR gate 100 causes the NOR gate 102 to develop at its output a signal of logic zero. Since the outputs of the NOT gate 103 and the flip-flop 107 are also logic zeroes, the AND gates 105 and 106 are blocked by a signal of logic zero applied from the output of the OR gate 104, with the result that the signals at the outputs 21 and 22 are logic zeroes. The logic circuit 6 (FIG. 2) receives in this case information indicative of the absence of significant changes in the duration of RR intervals.

On termination of the reset signal, the data on the relative durations of two adjacent RR intervals starts coming to the inputs 19 and 20 (FIG. 7). As long as the signals at these inputs differ from those at the second inputs of the Exclusive OR gates 100 and 101, respectively, the initial condition setting unit 18 will remain in the initial state, i.e. the signals at the outputs 21 and 22 will remain logic zeroes.

When the signals at the inputs 19 and 20 respectively coincide with those at the second inputs of the Exclusive OR gates 100 and 101, the outputs of the gates 100 and 101 will become logic zeroes and the NOR gate 102 will develop at its output a signal of logic one, which passes through the OR gate 104 and sets the flip-flop 107 to a logic one state. As a result, the OR gate 104 will constantly maintain at its output a signal of logic one causing the AND gates 105 and 106 to open and the signals from the inputs 19 and 20 to pass, respectively to the outputs 21 and 22.

If the switch 99 is set to the first position, the initial condition setting unit 18 will cause the signals from the inputs 19 and 20 to pass, respectively, to the outputs 21 and 22 only after the inputs 19 and 20 are simultaneously supplied with signals of logic one. In this case the signals at the first inputs of the Exclusive OR gates 100 and 101 will coincide with the signals at their second inputs set by the switch 99. The presence of signals of logic one at the inputs 19 and 20 indicates a significant lengthening of the last occurring RR interval in relation to the preceding interval (the inequalities (4) and (6) are satisfied).

When the switch 99 is set to the second position, the signal at the second input of the Exclusive OR gate 100 is a logic one and the signal at the second input of the Exclusive OR gate 101 is a logic zero. To switch the initial condition setting unit 18 to a conducting state, it is necessary for signals of logic one and zero to simultaneously appear at the inputs 19 and 20, respectively. These conditions are met when the inequalities (4) and (5) are satisfied, i.e. when a significant shortening of the last occurring RR interval in relation to the preceding interval is registered.

When the switch 99 (FIG. 7) is set to the third position, the input of the NOT gate 103 is supplied with a signal of logic zero. The signal of logic one from the output of the NOT gate 103 passes through the OR gate 104 and sets the flip-flop 107 to a logic one state providing application of an enabling signal of a logic one to the AND gates 105 and 106. Therefore, as soon as the switch 99 is set to the third position, the initial condition setting unit 18 passes any signal from the input 19 to the output 21 and from the input 20 to the output 22. Thus, by setting the initial conditions with the aid of the switch 99, the possibility of starting the diagnostic process with an irregular RR interval and drawing thereby a false conclusion is eliminated. The heart monitoring device begins to analyse the cardiac rhythm only after the appearance of RR intervals with a combination of durations typical of the person being examined.

FIG. 8 is a block diagram of a heart monitoring device which provides automatic check on the operation of the device basic units, whereby a more reliable diagnosis can be achieved. In this case the commands supplied from the timing unit 13 to other device units are shown in the drawings in brackets.

This device operates on the same principle as the device shown in FIG. 1. The operation of the heart monitoring device having an improved diagnosis reliability will be described below in reference to its distinguishing features, without detailed explanation of the common points described above.

The timing unit 13 (FIG. 8) generates commands (FIG. 9e), in response to which the following operations are performed:

$T_1$:
data from the counter 25 (FIG. 3) are stored into the register 29;
data from the counter 26 are stored into the register 30;
data from the counter 27 are stored into the shift register 32;
data from the reversible counter 28 are stored into the register 31;

$T_2$:
data from the counter 27 are stored into the register 114 and the reversible counter 28;
$\Delta RR_i$ is compared to $0.2 RR_i$ by the comparator 41;

$T_3$:
the counters 25, 26 and 27 are reset;
$RR_{i-1}$ is compared to $RR_i$ by the comparator 41;

$T_4$:
$RR_{i-2}$ is compared to $(RR_{i-1} - 0.6 \text{ s})$ by the comparator 41.

As a result of these operations performed on application of the commands $T_1$, $T_2$, $T_3$ and $T_4$ (FIG. 9e), the flip-flops 42, 43 and 44 (FIG. 3) are stored with data on the relation between the durations of three consecutive RR intervals.

On application of the command $T_5$, the pulse oscillator 109 (FIG. 8) and the monostable multivibrator 108 are started. The pulse oscillator 109 generates test pulses $C_t$ (FIG. 9c) at a frequency N times greater than that of the clock pulses C generated by the pulse oscillator 23 (FIG. 3). The pulses C and $C_t$ are supplied through the OR gate 119. The reversible counter 28 develops the test value of $\Delta RR_i$ by subtracting the test pulses $C_t$ (FIG. 9c) from the value of $RR_{i-1}$ stored into the counter 28 on application of the command $T_2$, until the monostable multivibrator 108 (FIG. 8) generates a control pulse $S_t$ (FIG. 9b), which stops the pulse oscillator 109 (FIG. 8).

The counter 25 (FIG. 3) reaches a count corresponding to one-fifth of the test interval $RR_i$. The number N is chosen such that the number of test pulses $C_t$ (FIG. 9e) occurring between the command $T_5$ and the control pulse $S_t$ (FIG. 9b) is sufficient to provide detection of the test arrhythmia by comparing the contents of the reversible counter 28 (FIG. 3) and the counter 25. The number N should be chosen on the basis of the minimum value of the real interval $RR_{i-1}$ stored into the reversible counter 28, so that when the device operates correctly, the inequality (4) is always satisfied during the check procedure.

Figure 9:
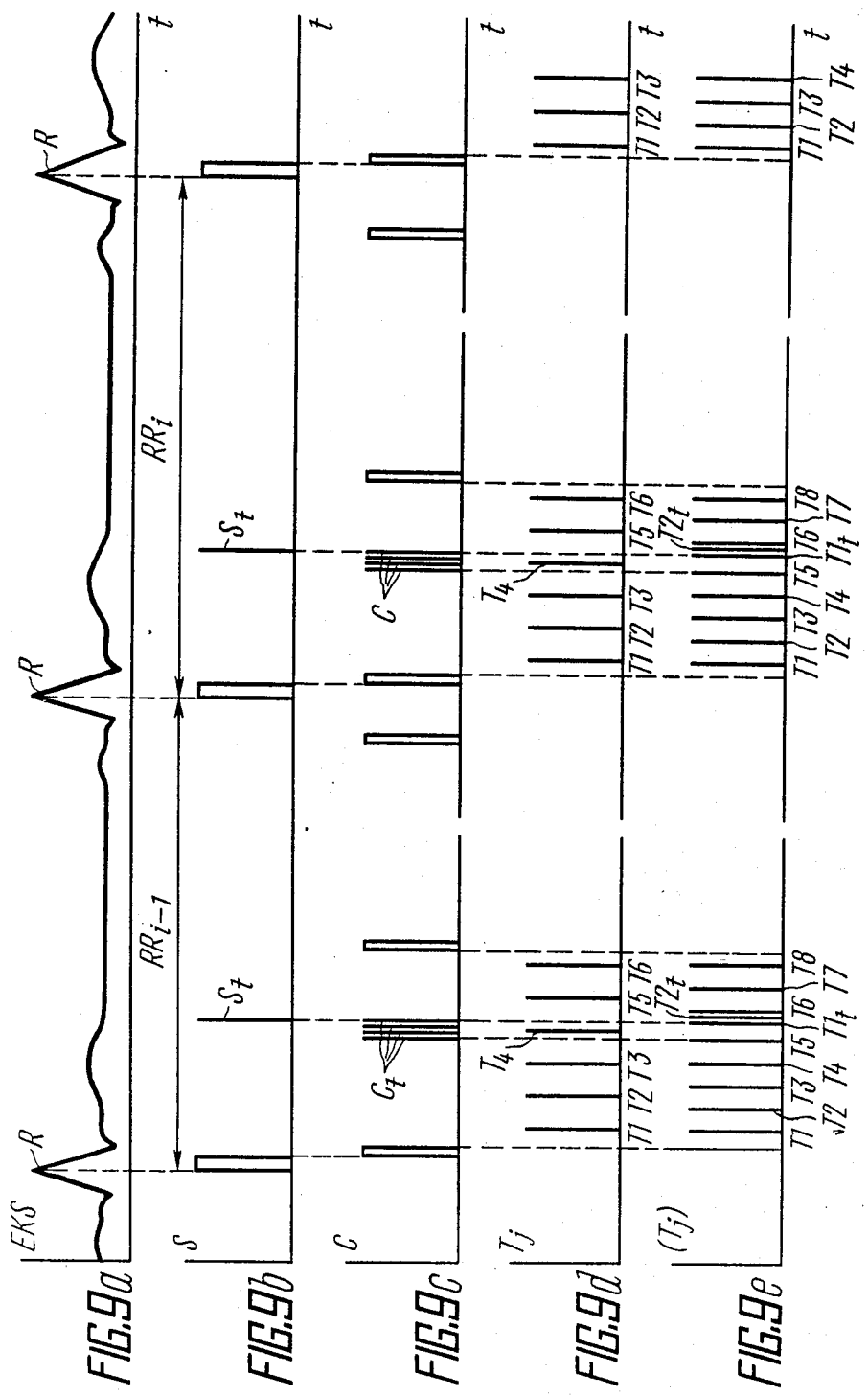
FIGS. 9a–9e are timing diagrams of the signals at the outputs of the units of the proposed heart monitoring device.

After the appearance of the control pulse $S_t$ (FIG. 9b), the timing unit 13 (FIG. 8) generates test commands $T_{1t}$ and $T_{2t}$ (FIG. 9e).

The command $T_{1t}$ is applied to the control inputs of the registers 29 and 31 (FIG. 3). This command controls the storage of data from the counter 25 into the register 29 (the test value of $0.2RR_i$) and from the reversible counter 28 into the register 31 (the test value of $\Delta RR_i$).

On application of the command $T_{2t}$ (FIG. 9e), the comparator 41 (FIG. 3) compares the test values of $\Delta RR_i$ and $0.2RR_i$, with the result being stored into the flip-flop 110 (FIG. 8). If the inequality (4) is satisfied, the flip-flop 110 is set to a logic one state confirming the operability of the device.

In this case the malfunction indicator 111 does not operate and the indication unit 12 (FIG. 6) is provided with an enabling voltage which is applied to the third inputs of the AND gates 76, 77, 78, 79, 80 and 81.

Since the OR gate 120 (FIG. 5) of the storage unit 11 is supplied from the inverted output of the flip-flop 110 with a signal of logic zero, there is no change in the storage unit 11.

On application of the command $T_6$ (FIG. 9e), the indication unit 12 (FIG. 8) counts the detected arrhythmias, the number of the arrhythmias being indicated by a corresponding indicator. The analysis of the cardiac rhythm is performed in the same way as in the circuit of FIG. 1.

On application of the command $T_7$ (FIG. 9e), the storage unit 11 (FIG. 8) is stored with the result of analysis of the cardiac rhythm obtained in the preceding cycle and provided by the logic circuit 6.

On application of the command $T_8$ (FIG. 9e), the following operations are performed:
the counters 25, 26 and 27 (FIG. 3) are reset;
data from the register 114 are transferred to the counter 28;
the flip-flop 110 (FIG. 8) is set to a logic one state.

Then the device is prepared for the next cycle of analysis of cardiac rhythm. The reversible counter 28 (FIG. 3) has a count corresponding to the duration of the preceding interval $RR_{i-1}$.

During application of commands from the timing unit 13 (FIG. 8), the OR gates 115, 116, 117 and 118 provide decoupling of signals at the outputs 14 of the timing unit 13.

If, on application of the test command $T_{2t}$, the inequality (4) is not satisfied, the flip-flop 110 (FIG. 8) assumes a logic zero state and turns on the malfunction indicator 111. The passage of data to the indicator 12 is inhibited. The storage unit 11 (FIG. 5) is supplied through the OR gate 120 with the reset signal, with the result that the storage unit 11 is stored with data corresponding to the presence of a normal cardiac rhythm in the preceding cycle of analysis.

Since the flip-flop 110 (FIG. 8) retains the state corresponding to malfunction until the command $T_8$ is applied, the application of the commands $T_6$ and $T_7$ produces no change in the states of the indication unit 12 and the storage unit 11. After a malfunction, the subsequent analysis of the cardiac rhythm is performed with reference to the normal rhythm.

Therefore, after each cycle of analysis of the cardiac rhythm, a check on the correctness of operation of the sensing unit 1 (FIG. 8), the ECG signal parameters determining unit 2 and the timing unit 13 is provided, which increases the reliability of data obtained with the aid of the heart monitoring device responding to the ECG signal taken from a person.

Thus the employment of the heart monitoring device provides for prolonged and continuous monitoring of various types of irregularities in the heart rate and cardiac rhythm under conditions associated with various kinds of vital activity of a healthy or sick person. This makes possible acquisition of objective information concerning the state of the cardiovascular system of the person being studied, during his active life, preventive or therapeutic treatment, rehabilitation and tests under loads. This also permits well-founded measures to be taken to control the effect of external factors influencing the heart action.

The small amount of data processed by the proposed device in the course of diagnostic process makes it possible to provide a device which is simple in design, small in size and reliable in operation. The proposed device has special design features which make a false diagnosis less likely and provide acquisition of most reliable data on the cardiac rhythm of the person being studied.

By using decimal code for indicating the number of the detected arrhythmias and by indicating the number of only most common irregularities in the cardiac rhythm of the person being studied, the proposed device makes possible quick reading and convenient analysis of the output data and provides for a compact design of the indication system.

By enabling any person to monitor his heart activity in proper time and under a wide variety of conditions occurring in everyday life, it is possible to reduce the number of dangerous terminal states leading to ventricular fibrillation and cardiac arrest and to provide decrease in mortality caused by cardiovascular disorders.

We claim:

1. A heart monitoring device for monitoring the heart activity of a person by using an ECG (electrocardiograph) signal comprising:
a sensing unit for detecting R-waves of said ECG signal characterizing the heart activity of the person, said sensing unit having an input supplied with said ECG signal, and an output;

an ECG signal parameters determining unit responsive to variation in relation between the durations of intervals between the R-waves of said ECG signal and having a data input connected to said output of said sensing unit, a plurality of control inputs, a reset input, a first output, a second output, and a third output, said ECG signal parameters determining unit being arranged to produce at said first output a first signal when the magnitude of the difference between the duration of the last occurring interval between the R-waves of said ECG signal and the duration of the interval between the R-waves immediately preceding the last occurring interval is smaller than a first predetermined percentage of the duration of the last occurring interval, and to produce at said first output a second signal when the magnitude of the difference between the last occurring interval between the R-waves of said ECG signal and the duration of the interval between the R-waves immediately preceding the last occurring interval is greater than, or equal to, said first predetermined percentage of the last occurring interval, said ECG signal parameters determining unit being arranged to produce at said second output a first signal when the duration of the last occurring interval between the R-waves of said ECG signal is smaller than the duration of the interval between the R-waves immediately preceding the last occurring interval, and to produce at said second output a second signal when the duration of the last occurring interval between the R-waves of said ECG signal is greater than, or equal to, the duration of the interval between the R-waves immediately preceding the last occurring interval, said ECG signal parameters determining unit being arranged to produce at said third output a first signal when the difference between the duration of the last occurring interval between the R-waves of said ECG signal and the duration of the interval between the R-waves immediately preceding the interval which immediately preceeds the last occurring interval is smaller than a second predetermined value, and to produce at said third output a second signal when the difference between the duration of the last occurring interval between the R-waves of said ECG signal and the duration of the interval between the R-waves immediately preceding the interval which immediately preceeds the last occurring interval is greater than, or equal to, said second predetermined value;

a logic circuit having a plurality of inputs and a plurality of outputs, a first input of said plurality of inputs being connected to said first output of said ECG signal parameters determining unit, a second input of said plurality of inputs being connected to said second output of said ECG signal parameters determining unit, and a third input of said plurality of inputs being connected to said third output of said ECG signal parameters determining unit;

a storage unit having a plurality of inputs respectively connected to corresponding outputs of said plurality of outputs of said logic circuit, a control input, a reset input, and a plurality of outputs respectively connected to corresponding remaining inputs of said plurality of inputs of said logic circuit;

an indication unit having a plurality of data inputs respectively connected to corresponding outputs of said plurality of outputs of said logic circuit, a reset input, and a control input;

a timing unit having an input connected to said output of said sensing unit, a first output connected to said control input of said storage unit, a second output connected to said control input of said indication unit, and a plurality of outputs respectively connected to corresponding control inputs of said ECG signal parameters determining unit, to supply said control inputs of said ECG signal parameters determining unit, said storage unit and said indication unit with signals during each interval between the R-waves of said ECG signal; and a reset unit having an output connected to said reset inputs of said ECG signal parameters determining unit, said indication unit and said storage unit;

said logic circuit being arranged to produce at said outputs thereof a first, second, third, fourth, fifth, sixth, seventh or eighth combination of signals, said logic circuit being arranged to produce at said outputs thereof said first combination of signals when said first input of said logic circuit is supplied with said second signal from said first output of said ECG signal parameters determining unit, said second input of said logic circuit is supplied with said first signal from said second output of said ECG signal parameters determining unit and said storage unit is stored with a code corresponding to said first, third or eighth combination of signals at said outputs of said logic circuit, said logic circuit being arranged to produce at said outputs thereof said first combination of signals when said first input of said logic circuit is supplied with said first signal from said first output of said ECG signal parameters determining unit and said storage unit is stored with a code corresponding to said first, third or eighth combination of signals at said outputs of said logic circuit, said logic circuit being arranged to produce at said outputs thereof said second combination of signals when said first input of said logic circuit is supplied with said second signal from said first output of said ECG signal parameters determining unit, said second input of said logic circuit is supplied with said second signal from said second output of said ECG signal parameters determining unit and said storage unit is stored with a code corresponding to said first, third or eighth combination of signals at said outputs of said logic circuit, said logic circuit being arranged to produce at said outputs thereof said third combination of signals when said first input of said logic circuit is supplied with said second signal from said first output of said ECG signal parameters determining unit, said second input of said logic circuit is supplied with said first signal from said second output of said ECG signal parameters determining unit and said storage unit is stored with a code corresponding to said seventh combination of signals at said outputs of said logic circuit, said logic circuit being arranged to produce at said outputs thereof said fourth combination of signals when said first input of said logic circuit is supplied with said second signal from said first output of said ECG signal parameters determining unit, said second input of said logic circuit is supplied with said second signal from said second output of said ECG signal parameters determining unit and said storage unit is stored with a code corresponding to said seventh combination of signals at said outputs of said logic circuit, said logic circuit being arranged to produce at said outputs thereof said fourth combination of signals when said first input of said logic circuit is supplied with said second signal from said first output of said ECG signal parameters determining unit, said second input of said logic circuit is supplied with said second signal from said second output of said ECG signal parameters determining unit and said storage unit is stored with a code corresponding to said sixth combination of signals at said outputs of said logic circuit, said logic circuit being arranged to produce at said outputs thereof said fifth combination of signals when said first input of said logic circuit is supplied with said second signal from said first output of said ECG signal parameters determining unit, said second input of said logic circuit is supplied with said second signal from said second output of said ECG signal parameters determining unit and said storage unit is stored with a code corresponding to said fourth or fifth combination of signals at said outputs of said logic circuit, said logic circuit being arranged to produce at said outputs thereof said fifth combination of signals when said first input of said logic circuit is supplied with said first signal from said first output of said ECG signal parameters determining unit and said storage unit is stored with a code corresponding to said fourth or fifth combination of signals at said outputs of said logic circuit, said logic circuit being arranged to produce at said outputs thereof said sixth combination of signals when said first input of said logic circuit is supplied with said second signal from said first output of said ECG signal parameters determining unit, said second input of said logic circuit is supplied with said first signal from said second output of said ECG signal parameters determining unit and said storage unit is stored with a code corresponding to said fourth or fifth combination of signals at said outputs of said logic circuit, said logic circuit being arranged to produce at said outputs thereof said seventh combination of signals when said first input of said logic circuit is supplied with said second signal from said first output of said ECG signal parameters determining unit, said second input of said logic circuit is supplied with said second signal from said second output of said ECG signal parameters determining unit and said storage unit is stored with a code corresponding to said second combination of signals at said outputs of said logic circuit, said logic circuit being arranged to produce at said outputs thereof said seventh combination of signals when said first input of said logic circuit is supplied with said first signal from said first output of said ECG signal parameters determining unit and said storage unit is stored with a code corresponding to said second combination of signals at said outputs of said logic circuit, said logic circuit being arranged to produce at said outputs thereof said seventh combination of signals when said first input of said logic circuit is supplied with said second signal from said first output of said ECG signal parameters determining unit, said second input of said logic circuit is supplied with said first signal from said second output of said ECG signal parameters determining unit, said third input of said logic circuit is supplied with said second signal from said third output of said ECG signal parameters determining unit and said storage unit is stored with a code corresponding to said second combination of signals at said outputs of said logic circuit, said logic circuit being arranged to produce at said outputs thereof said seventh combination of signals when said first input of said logic circuit is supplied with said first signal from said first output of said ECG signal parameters determining unit and said storage unit is stored with a code corresponding to said seventh combination of signals at said outputs of said logic circuit, said logic circuit being arranged to produce at said outputs thereof said seventh combination of signals when said first input of said logic circuit is supplied with said second signal from said first output of said ECG signal parameters determining unit, said second input of said logic circuit is supplied with said first signal from said second output of said ECG signal parameters determining unit and said storage unit is stored with a code corresponding to said sixth combination of signals at said outputs of said logic circuit, said logic circuit being arranged to produce at said outputs thereof said seventh combination of signals when said first input of said logic circuit is supplied with said first signal from said first output of said ECG signal parameters determining unit and said storage unit is stored with a code corresponding to said sixth combination of signals at said outputs of said logic circuit, said logic circuit being arranged to produce at said outputs thereof said eighth combination of signals when said first input of said logic circuit is supplied with said second signal from said first output of said ECG signal parameters determining unit, said second input of said logic circuit is supplied with said first signal from said second output of said ECG signal parameters determining unit, said third input of said logic circuit is supplied with said first signal from said third output of said ECG signal parameters determining unit and said storage unit is stored with a code corresponding to said second combination of signals at said outputs of said logic circuit; and said indication unit being arranged to indicate a grouped extrasystole when said logic circuit produces at said outputs thereof said first combination of signals, to indicate a single extrasystole when said logic circuit produces at said outputs thereof said third combination of signals, to indicate a block when said logic circuit produces at said outputs thereof said fourth combination of signals, to indicate a dangerous block when said logic circuit produces at said outputs thereof said fifth combination of signals, to indicate a bigeminal extrasystole when said logic circuit produces at said outputs thereof said eighth combination of signals, and to indicate a normal cardiac rhythm when said logic circuit produces at said outputs thereof said seventh combination of signals.

2. A heart monitoring device according to claim 1, further comprising an initial condition setting unit arranged to be set to one of three positions and having a first input connected to said first output of said ECG signal parameters determining unit, a second input connected to said second output of said ECG signal parameters determining unit, a reset input connected to said output of said reset unit, a first output connected to said first input of said plurality of inputs of said logic circuit, and a second output connected to said second input of said plurality of inputs of said logic circuit, said initial condition setting unit, when set to a first of said three positions, producing at said first output thereof a signal equal to said first signal at said first output of said ECG signal parameters determining unit and at said second output of said initial parameters determining unit a signal equal to said first signal at said second output of said ECG signal parameters determining unit, if said first input of said initial condition setting unit is supplied with said first signal from said first output of said ECG signal parameters determining unit and said second input of said initial condition setting unit is supplied with said first signal from said second output of said ECG signal parameters determining unit, or if said first input of said initial condition setting unit is supplied with said firt signal from said first output of said ECG signal parameters determining unit and said second input of said initial condition setting unit is supplied with said second signal from said second output of said ECG signal parameters determining unit, or if said first input of said initial condition setting unit is supplied with said second signal from said first output of said ECG signal parameters determining unit and said second input of said initial condition setting unit is supplied with said first signal from second output of said ECG signal parameters determining unit, until said first input of said initial condition setting unit is supplied for the first time with said second signal from said first output of said ECG signal parameters determining unit and said second input of said initial condition setting unit is simultaneously supplied with said second signal from said second output of said ECG signal parameters determining unit, whereupon said initial condition setting unit produces at said first and second outputs thereof signals respectively equal to the signals at said first and second inputs of said initial condition setting unit, said initial condition setting unit, when set to a second of said three positions, producing at said first output thereof a signal equal to said first signal at said first output of said ECG signal parameters determining unit and at said second output of said initial condition setting unit a signal equal to said first signal at said second output of said ECG signal parameters determining unit, if said first input of said initial condition setting unit is supplied with said first signal from said first output of said ECG signal parameters determining unit and said second input of said initial condition setting unit is supplied with said first signal from said second output of said ECG signal parameters determining unit, or if said first input of said initial condition setting unit is suplied with said first signal from said first output of said ECG signal parameters determining unit and said second input of said initial condition setting unit is supplied with said second signal from said second output of said ECG signal parameters determining unit, or if said first input of said initial condition setting unit is supplied with said second signal from said first output of said ECG signal parameters determining unit and said second input of said initial condition setting unit is supplied with said second signal from said second output of said ECG signal parameters determining unit, until said first input of said initial condition setting unit is supplied for the first time with said second signal from said first output of said ECG signal parameters determining unit and said second input of said initial condition setting unit is simultaneously supplied with said first signal from said second output of said ECG signal parameters determining unit, whereupon said initial condition setting unit produces at said first and second outputs thereof signals respectively equal to the signals at said first and second inputs of said initial condition setting unit, said initial condition setting unit, when set to a third of said three positions, producing at said first and second outputs thereof signals respectively equal to the signals at said first and second inputs of said initial condition setting unit.

3. A heart monitoring device according to claim 1, wherein said logic circuit comprises:
- a first AND gate having a first input connected to said first output of said ECG signal parameters determining unit, a second input connected to said second output of said ECG signal parameters determining unit, and an output;
- a second AND gate having an input connected to said first output of said ECG signal parameters determining unit, an inverting input connected to said second output of said ECG signal parameters determining unit, and an output;
- a NOT gate having an input connected to said first output of said ECG signal parameters determining unit, and an output;
- a third AND gate having a first input connected to said output of said second AND gate, a second input, and an output;
- a fourth AND gate having a first input connected to said output of said NOT gate, a second input, and an output;
- a fifth AND gate having a first input connected to said output of said first AND gate, a second input, and an output;
- a sixth AND gate having a first input connected to said output of said second AND gate, a second input, and an output;
- a seventh AND gate having a first input connected to said output of said second AND gate, a second input, and an output;
- an eighth AND gate having a first input connected to said output of said first AND gate, a second input, and output;
- a ninth AND gate having a first input connected to said output of said first AND gate, a second input, and an output;
- a tenth AND gate having a first input connected to said output of said first AND gate, a second input, and an output;
- an eleventh AND gate having a first input connected to said output of said NOT gate, a second input, and an output;
- a twelfth AND gate having a first input connected to said output of said second AND gate, a second input, and an output;
- a thirteenth AND gate having a first input connected to said output of said NOT gate, a second input, and output;
- a fourteenth AND gate having a first input connected to said output of said first AND gate, a second input, and an output;
- a fifteenth AND gate having a first input connected to said output of said second AND gate, a second input, and an output;

a sixteenth AND gate having a first input connected to said output of said NOT gate, a second input, and an output;

a seventeenth AND gate having a first input connected to said output of said NOT gate, a second input, and an output;

an eighteenth AND gate having an input connected to said output of said sixth AND gate, an inverting input connected to said third output of said ECG signal parameters determining unit, and an output;

a nineteenth AND gate having a first input connected to said third output of said ECG signal parameters determining unit, a second input connected to said output of said sixth AND gate, and an output;

a first OR gate having a first input connected to said output of said third AND gate, a second input connected to said output of said fourth AND gate, and an output;

a second OR gate having a first input connected to said output of said eighth AND gate, a second input connected to said output of said ninth AND gate, and an output;

a third OR gate having a first input connected to said output of said tenth AND gate, a second input connected to said output of said eleventh AND gate, and an output; and a fourth OR gate having a first input connected to said output of said thirteenth AND gate, a second input connected to said output of said fourteenth AND gate, a third input connected to said output of said fifteenth AND gate, a fourth input connected to said output of said sixteenth AND gate, a fifth input connected to said output of said seventeenth AND gate, a sixth input connected to said output of said nineteenth AND gate, and an output;

said storage unit comprises:

a first OR gate having a first input connected to said output of said first OR gate of said logic circuit, a second input connected to said output of said seventh AND gate of said logic circuit, a third input connected to said output of said eighteenth AND gate of said logic circuit, and an output;

a second OR gate having a first input connected to said output of said second OR gate of said logic circuit, a second input connected to said output of said third OR gate of said logic circuit, and an output;

a first flip-flop having a data input connected to said output of said first OR gate of said storage unit, a clock input connected to said first output of said timing umit, a reset input connected to said output of said reset unit, and an output connected to said second inputs of said third, fourth and fifth AND gates of said logic circuit;

a second flip-flop having a data input connected to said output of said fifth AND gate of said logic circuit, a clock input connected to said first output of said timing unit, a reset input connected to said output of said reset unit, and an output connected to said second inputs of said sixth, thirteenth and fourteenth AND gates of said logic circuit;

a third flip-flop having a data input connected to said output of said second OR gate of said storage unit, a clock input connected to said first output of said timing unit, a reset input connected to said output of said reset unit, and an output connected to said second inputs of said tenth, eleventh and twelfth AND gates of said logic circuit;

a fourth flip-flop having a data input connected to said output of said twelfth AND gate of said logic circuit, a clock input connected to said first output of said timing unit, a reset input connected to said output of said reset unit, and an output connected to said second inputs of said eighth, fifteenth and sixteenth AND gates of said logic circuit; and a fifth flip-flop having a data input connected to said output of said fourth OR gate of said logic circuit, a clock input connected to said first output of said timing unit, a set input connected to said output of said reset unit, and an output connected to said second inputs of said seventh, ninth and seventeenth AND gates of said logic circuit; and said indication unit comprises:

a first AND gate having a first input connected to said output of said fourth OR gate of said logic circuit, a second input connected to said second output of said timing unit, and an output;

a second AND gate having a first input connected to said output of said first OR gate of said logic circuit, a second input connected to said second output of said timing unit, and an output;

a third AND gate having a first input connected to said output of said seventh AND gate of said logic circuit, a second input connected to said second output of said timing unit, and an output;

a fourth AND gate having a first input connected to said output of said second OR gate of said logic circuit, a second input connected to said second output of said timing unit, and an output;

a fifth AND gate having a first input connected to said output of said third OR gate of said logic circuit, a second input connected to said second output of said timing unit, and an output;

a sixth AND gate having a first input connected to said output of said eighteenth AND gate of said logic circuit, a second input connected to said second output of said timing unit, and an output;

a first counter having a counting input connected to said output of said second AND gate of said indication unit, a reset input connected to said output of said reset unit, and a plurality of outputs;

a second counter having a counting input connected to said output of said third AND gate of said indication unit, a reset input connected to said output of said reset unit, and a plurality of outputs;

a third counter having a counting input connected to said output of said fourth AND gate of said indication unit, a reset input connected to said output of said reset unit, and a plurality of outputs;

a fourth counter having a counting input connected to said output of said fifth AND gate of said indication unit, a reset input connected to said output of said reset unit, and a plurality of outputs;

a fifth counter having a counting input connected to said output of said sixth AND gate of said indication unit, a reset input connected to said output of said reset unit, and a plurality of outputs;

a first indicator control unit having an input connected to said output of said first AND gate of said indication unit, and an output;

a second indicator control unit having a plurality of inputs respectively connected to corresponding outputs of said first counter, a plurality of outputs;

a third indicator control unit having a plurality of inputs respectively connected to corresponding outputs of said second counter, and a plurality of outputs;

a fourth indicator control unit having a plurality of inputs respectively connected to corresponding outputs of said third counter, and a plurality of outputs;

a fifth indicator control unit having a plurality of inputs respectively connected to corresponding outputs of said fourth counter, and a plurality of outputs;

a sixth indicator control unit having a plurality of inputs respectively connected to corresponding outputs of said fifth counter, and a plurality of outputs;

a first indicator indicating a normal cardiac rhythm and having an input connected to said output of said first indicator control unit;

a second indicator indicating the number of grouped extrasystoles and having a plurality of inputs respectively connected to corresponding outputs of said second indicator control unit;

a third indicator indicating the number of single extrasystoles and having a plurality of inputs respectively connected to corresponding outputs of said third indicator control unit;

a fourth indicator indicating the number of blocks and having a plurality of inputs respectively connected to corresponding outputs of said fourth indicator control unit;

a fifth indicator indicating the number of dangerous blocks and having a plurality of inputs respectively connected to corresponding outputs of said fifth indicator control unit; and a sixth indicator indicating the number of bigeminal extrasystoles and having a plurality of inputs respectively connected to corresponding outputs of said sixth indicator control unit.

4. A heart monitoring device according to claim 2, wherein said initial condition setting unit comprises:

a first Exclusive OR gate having a first input constituting said first input of said initial condition setting unit, a second input, and an output;

a second Exclusive OR gate having a first input constituting said second input of said initial condition setting unit, a second input, and an output;

a NOR gate having a first input connected to said output of said first Exclusive OR gate, a second input connected to said output of said second Exclusive OR gate, and an output;

a NOT gate having an input connected to said second input of said first Exclusive OR gate, and an output;

an OR gate having a first input connected to said output of said NOR gate, a second input connected to said output of said NOT gate, a third input, and an output;

a first AND gate having a first input connected to said first input of said first Exclusive OR gate, a second input connected to said output of said OR gate, and an output constituting said first output of said initial condition setting unit;

a second AND gate having a first input connected to sid first input of said second Exclusive OR gate, a second input connected to said output of said OR gate and an output constituting said second output of said initial condition setting unit;

a flip-flop having a set input connected to said output of said OR gate, a reset input connected to said output of said reset unit, and an output connected to said third input of said OR gate; and a switch arranged to supply said second input of said first Exclusive OR gate with a signal equal to said second signal at said first output of said ECG signal parameters determining unit and said second input of said second Exclusive OR gate with a signal equal to said second signal at said second output of said ECG signal parameters determining unit, when said switch is in a first position, to supply said second input of said first Exclusive OR gate with a signal equal to said second signal at said first output of said ECG signal parameters determining unit and said second input of said second Exclusive OR gate with a signal equal to said first signal at said second output of said ECG signal parameters determining unit, when said switch is in a second position, and to supply said input of said NOT gate with a signal equal to said first signal at said first output of said ECG signal parameters determining unit when said switch is in a third position.

5. A heart monitoring device according to claim 1, wherein said ECG signal parameters determining unit is further provided with a second data input and with an additional output;

said storage unit is further provided with a second reset input;

said indication unit is further provided with an indication permitting input;

said timing unit is further provided with a second input and with an additional output, said heart monitoring device further comprising:

a monostable multivibrator having an input connected to said additional output of said timing unit, and an output connected to said second input of said timing unit;

a pulse oscillator having an enable input connected to said additional output of said timing unit, a disable input connected to said output of said monostable multivibrator, and an output connected to said second data input of said ECG signal parameters determining unit;

a flip-flop having a data input connected to said additional output of said ECG signal parameters determining unit, a set input, a reset input, an output connected to said indication permitting input of said indication unit, and an inverted output connected to said second reset input of said storage unit, said set input and said reset input being respectively connected to corresponding two outputs of said plurality of outputs of said timing unit; and a malfunction indicator having an input connected to said inverted output of said flip-flop.

* * * * *